United States Patent [19]
Iwata et al.

[11] 3,946,033
[45] Mar. 23, 1976

[54] PROCESS FOR THE PREPARATION OF HYDANTOIN DERIVATIVES

[75] Inventors: Kaoru Iwata; Shigeyoshi Hara, both of Hino, Japan

[73] Assignee: Teijin Ltd., Osaka, Japan

[22] Filed: Nov. 20, 1973

[21] Appl. No.: 417,566

[30] Foreign Application Priority Data
Nov. 24, 1972  Japan.............................. 47-117096
Dec. 18, 1972  Japan.............................. 47-126191

[52] U.S. Cl. ............................................. 260/309.5
[51] Int. Cl.² ....................................... C07D 233/54
[58] Field of Search ................................. 260/309.5

[56]  References Cited
UNITED STATES PATENTS
3,676,456  7/1972  Gruenfeld......................... 260/309.5
3,755,350  8/1973  Sauli................................ 260/309.5

*Primary Examiner*—G. Thomas Todd
*Attorney, Agent, or Firm*—Sherman & Shalloway

[57]  ABSTRACT

Hydantoin derivatives are produced by reacting
1. a glycine derivative,
2. a primary amine, and
3. a diaryl carbonate Thus, various kinds of hydantoin derivatives can be obtained without using an isocyanate.

11 Claims, No Drawings

PROCESS FOR THE PREPARATION OF HYDANTOIN DERIVATIVES

This invention relates to a novel process for the preparation of hydantoin derivatives.

More particularly, the invention relates to a novel process for the preparation of hydantoin derivatives which contain in their molecules at least one hydantoin ring (H) of the formula,

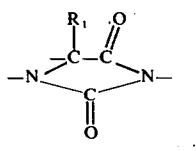   (H)

in which $R_1$ is hydrogen atom or a monovalent organic radical.

It is known to produce various α-amino acids through the steps of condensing hydantoins with, for example, various aldehydes, and hydrolyzing the condensation products, this is conventionally referred to as the preparation of α-amino acids by hydantoin process and has been practiced on industrial scales. Various substituted hydantoins are also known to be useful as pesticides, medicines, or intermediate materials thereof.

Again, the hydantoin derivatives containing at least two reactive groups such as carboxyl, hydroxyl, and primary amino groups serve as the starting materials in the production of various hydantoin ring-containing polymers some of which are known for their high thermal stability.

The following are typical of the known processes for the preparation of hydantoin derivatives:

(i) a process wherein amino acid or esters thereof are reacted with cyanate. This process can be expressed by the equation (i) below, taking the example of glycine as the amino acid.

$H_2N-CH_2-COOE + MCNO$

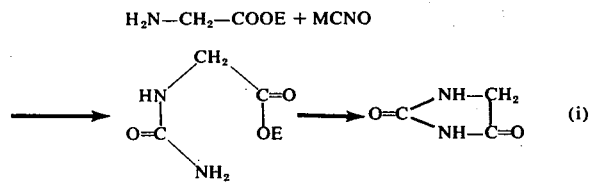   (i)

(in which E is hydrogen atom or a lower alkyl group, and M is an alkali metal).

(ii) a process wherein a cyanohydrin of aldehyde or ketone is heated with ammonium carbonate. The process can be expressed, for example, by the reaction formula (ii) below:

$E'-\overset{E}{\underset{|}{C}}=O + HCN$

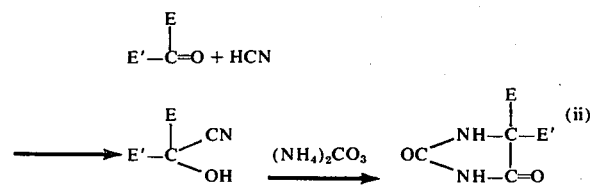   (ii)

(in which E is hydrogen atom or a lower alkyl group, and E' stands for a lower alkyl group).

(iii) a process in which an amino acid or a functional derivative thereof is reacted with an isocyanate or a compound which forms isocyanate during the reaction, such as a phenylurethane. The process can be expressed, for example, by the reaction formula (iii) below:

$E''NH-CH_2-COOE + E'''NCO$

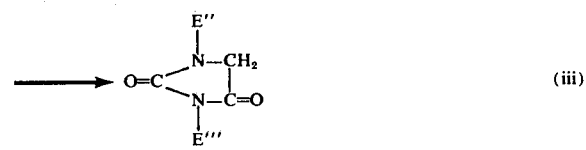   (iii)

(in which E, E'', and E''' may be the same or different, and each denotes hydrogen atom or a lower hydrocarbon residue).

The foregoing processes, however, are severely limited in their industrial applications, because they use either very toxic cyanic acid or highly reactive and toxic isocyanates and consequently require cumbersome considerations for appropriate equipment. Furthermore, isocyanates are normally manufactured through the reaction of the corresponding amines with phosgene which is again highly toxic. Therefore the utilizable types of isocyanates are extremely limited.

In the attempts to make hydantoin derivatives containing, for example, carboxyl, or hydroxyl groups, by the above process (iii) using an isocyanate, the isocyanate would react with the named reactive groups unless the reactive groups are inactivated in advance by way of protective groups. After the hydantoin formation through the reaction with an isocyanate; the protective groups must be split off from the product. Thus the process becomes objectionably complex and industrially disadvantageous.

The object of the present invention, accordingly, is to provide a novel process for easy preparation of hydantoin derivatives through a single stage reaction, without using cyanic acid or isocyanates.

Another object of the present invention is to provide a novel process whereby hydantoin derivatives containing any desired number of reactive groups such as carboxyl, or hydroxyl groups can be directly formed without the preceding protection of such reactive groups.

A further object of the invention is to provide a process for synthesizing a wide variety of hydantoin derivatives containing versatile substituent groups, with high economical advantage.

Still many other objects and advantages of the invention will become apparent from the following detailed description.

The foregoing objects and advantages of the invention are achieved by mutually reacting 1. a glycine derivative (I) containing at least one glycine residue (G) of the formula,

   (G)

in which $R_1$ is hydrogen atom or a monovalent organic radical, and

X is selected from a moiety of the formula, —OA, —SA, —NHA, and —N(A)$_2$, (A being hydrogen atom or a monovalent organic radical), with 2. an amine (II) containing at least one primary amino group of the formula,

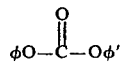

and 3. a diaryl carbonate (III) of the formula (III) below,

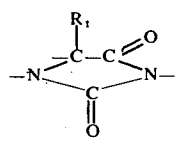

in which $\phi$ and $\phi'$ may be same or different, and each denotes a monovalent aromatic group.

Upon reacting the above-specified three components, a hydantoin derivative (IV) containing in its molecule at least one hydantoin ring (H) of the formula,

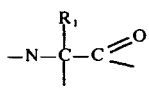

in which $R_1$ has the same definition as that previously given as to the formula (G) is formed.

The glycine derivatives (I) employed as one of the starting materials in the present invention may be any of such compounds containing in their molecules at least one glycine residue (G) of the formulae (G) as aforesaid, and which can retain the glycine skeleton ($G_1$) of the formula $$-N-\overset{R_1}{\underset{|}{C}}-C\overset{\nearrow O}{\underset{\searrow}{}} \qquad (G_1)$$

with stability, under the reaction conditions of the subject process.

Also the sole essential requirement for the primary amine (II) is that the compound must contain at least one primary amino group, (—NH$_2$). Therefore, ammonia and any other primary organic amines can be satisfactorily used, and in this specification the term "amine" is used in the sense inclusive of ammonia. It is required for the amines that they can at least retain the —NH— group with stability, under the reaction conditions of this invention. However, in case of using polyamines containing no less than two primary amino groups (—NH$_2$), organic amines in which the two primary amino groups at the minimum are linked through two carbon atoms are apt to form cyclic compounds with aforementioned diaryl carbonate (III) alone, interfering with the hydantoin ring-forming reaction of the three reactants including the glycine derivatives (I). Therefore, use of such organic polyamines should be avoided.

In short, according to the invention the active sites indicated with the triangular marks below of the formula (I), —NH$_2$, and the formula (III) mutually react to form a hydantoin ring, through the mechanism as illustrated by the formula (1) below, and therefore the experts in the art can easily select and determine the specific types and quantities of the glycine derivative (I), amine (II), and diaryl carbonate (III) to be employed.

Reaction Formula (1)

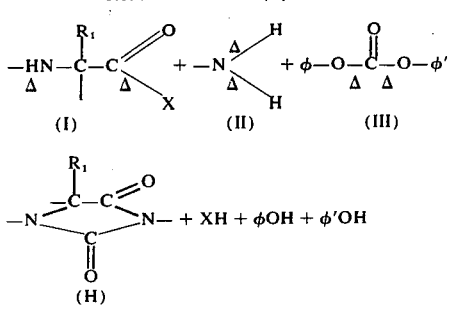

According to the invention, therefore, the glycine derivative (I) and amine (II) of the quantities as will make the glycine residue (G) in the former and primary amino group(s) in the latter substantially equimolar, and at least equimolar to the glycine residue (G) of diaryl carbonate (III), are used for the reaction of aforespecified three reactants, and upon the reaction the object hydantoin derivative (IV) is formed. Such reaction of the invention can progress in the absence of solvent or in the presence of an inert solvent, by heating the three starting materials (I), (II), and (III) together.

The heating temperature should be sufficient to allow the splitting off of the phenols of the formula $\phi$OH or $\phi'$OH, and water, alcohols, hydrogen sulfide, mercaptans, primary and secondary amines, and ammonia, etc., which can be covered by the formula XH.

Thus, according to the invention, for example, (1) a glycine derivative of the formula (I-1) or (I-2) below,

or

(in the above formulae, $R_1$ and X have the same definitions as those given as to the formula G, $R_2$ and $R_3$ may be same or different and each denotes hydrogen atom or a monovalent organic radical, $l$ is a positive integer of 1 to 5, and R is hydrogen atom or an $l$-valent organic radical), 2. an amine of the formula (II-1),

(in which m is a positive integer of 1 to 5, and W is hydrogen atom or an m-valent organic radical), and 3. a diaryl carbonate (III) of the formula (III),

(in which the definitions of φ and φ' are same to those already given)
are so selected that 4. either one or both of $l$ and $m$ should be 1, and mutually reacted to form any of the hydantoin derivatives of the formulae,

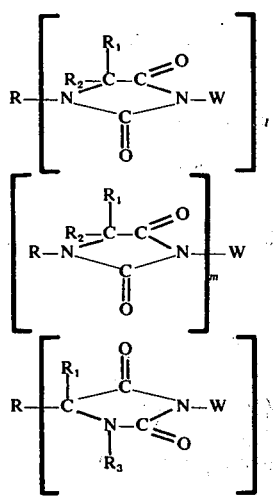

and

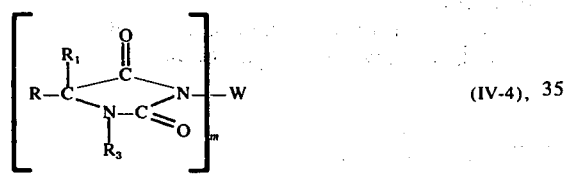

(in which above formulae, $R_1$, $R_2$, $R_3$, R, W, $l$, and $m$ have the same definitions as already given,
the formulae IV-1 and IV-2, and the formulae IV-3 and IV-4 being the same, respectively, when both $l$ and $m$ are 1,
when $l$ is 2 – 5 and $m$ equals 1, the product being expressed by the formula IV-1 or IV-3, and when $l$ equals 1 and $m$ is 2 to 5, the product being expressed by the formula IV-2 or IV-4).

As shown above, the glycine derivatives to be used in this invention can be classified into the typical two groups which are covered by the formulae I-1 and I-2. The structure of the formed hydantoin derivative (IV) thus differs depending on which group of the glycine derivative is employed, particularly when either $l$ or $m$ is no less than 2 (in that case, the other of $l$ or $m$ being 1).

In the above-described process, for example, if $l$ is 2 and $m$ is 1, or $l$ is 1 and $m$ is 2, hydantoin derivatives containing two symmetric hydantoin rings (H) are obtained.

In preferred embodiments of the invention, glycine derivatives (I-1a or I-2a) of the formulae (I-1) or (I-2) in which the R-denotes the formulae (D) below:

in which $R_4$ is a $(l+P)$ valent hydrocarbon residue or a hydrocarbon residue containing at least one member of the group consisting of oxygen, nitrogen, sulfur, phosphorus and silicon, the $(l+P)$ valency bonding with the carbon atoms, $F_1$ is at least one element or radical selected from the group consisting of halogen atoms, nitro, nitrile, tertiary amino,

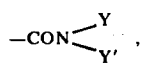

—OY, —SY, —COY, —OCOY, and —COOY radicals, Y and Y' being either the same or different and each denoting hydrogen atom or a monovalent organic radical, and
P is a positive integer of 0 to 10,
and/or, as the amines of previously given formula (II-1), the amines of formula (II-2) below,

in which
$W_1$ is a $(m + q)$ valent hydrocarbon residue, or a hydrocarbon residue containing at least one member of the group consisting of oxygen, nitrogen, sulfur, phosphorus and silicon, the $(m+q)$ valency bonding with the carbon atoms,
$F_2$ denotes at least one element or radical of the group consistitng of halogen atoms, nitro, nitrile, tertiary amino,

—OY, —SY, —COY, —OCOY, and —COOY radicals, Y and Y' being same or different and each standing for hydrogen atom or a monovalent organic radical,
$q$ is a positive integer of 0 to 10, and
$m$ has the same definition as already given,
are used to form hydantoin derivatives (IV-1, IV-2, IV-3, or IV-4) containing various substituents, particularly functional substituents.

In another preferred embodiment (A) of the present invention, (1) a glycine derivative of the formula (I-1b) or (I-2b)

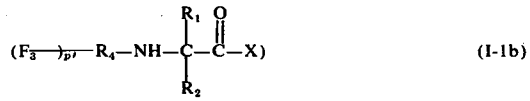

in which
$(F_3)_{p'}$ stands for a hydroxyl group (—OH) or one or two —COOY, in the last case the two —COOY's being linked with the two adjacent carbon atoms in $R_4$, respectively, $R_1$, $R_2$, $R_4$, X, and Y have the same definitions as already given, and p' represents a positive integer of 1 or 2, or

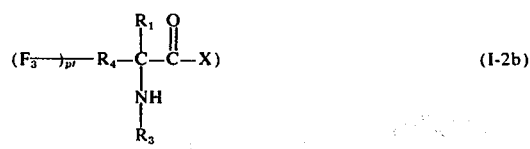

in which (F₃)ₚ stands for a hydroxyl group (—OH) or one or two —COOY, in the last case the two —COOY's being linked with the two adjacent carbon atoms in R₄, respectively, and p', R₁, R₃, R₄, X, and Y have the same definitions as already given, 2. a primary amine of the formula (II-3),

  (II-3)

in which (F₄)_q stands for a hydroxyl group (—OH) or one or two —COOY, in the last case the two —COOY's being linked with the two adjacent carbon atoms in W₁, respectively, and W₁, and Y have the same definitions as already given, and q' represents a positive integer of 1 or 2, and 3. diaryl carbonate of the formula (III)

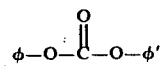  (III)

in which

φ and φ' have the same definitions as already given, are mutually reacted to form a difunctional hydantoin derivative of the formulae (IV-5) or (IV-6),

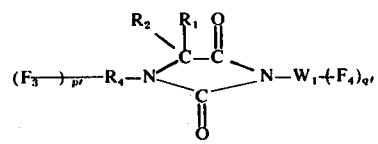  (IV-5)

or

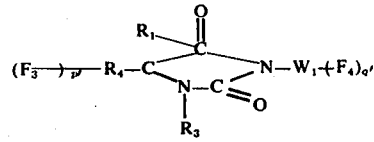  (IV-6)

in both of which

R₁, R₂, R₃, R₄, W₁, (F₃)_{p'} and (F₄)_{q'} have the same definitions as already given, which contains two functional groups selected from the group consisting of hydroxyl group, carboxyl group, and ester groups thereof.

According to still another embodiment (B) of the present invention, 1. a glycine derivative of the formula (I-1b) or (I-2b),

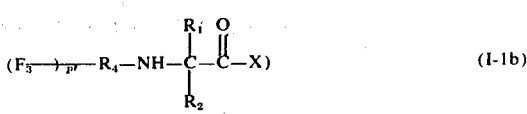  (I-1b)

in which

R₁, R₂, R₄, X, and (F₃)_q have the same definitions as already given, or

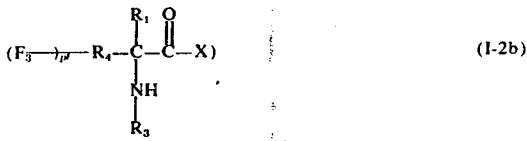  (I-2b)

in which

R₁, R₃, R₄, X, and (F₃)_{p'} have the same definitions as already given, 2. a primary diamine of the formula (II-4) below,

H₂N — W₂ — NH₂  (II-4)

in which

W₂ stands for a divalent organic radical, and 3. diaryl carbonate of the formula (III),

  (III)

are reacted at such a quantitative ratio that substantially 2 mols of the glycine derivative of formula (I-1b) or (I-2b) is used per mol of the primary diamine, to form a difunctional hydantoin derivative of the formula (IV-7),

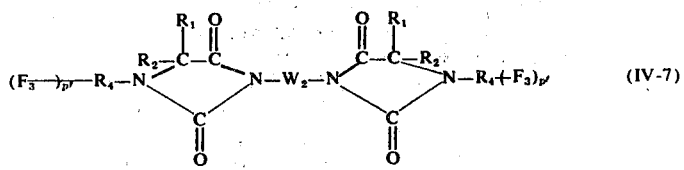  (IV-7)

or of the formula (IV-8),

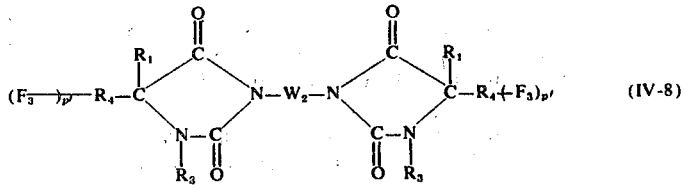  (IV-8)

in which

R₁, R₂, R₃, R₄, W₂, and (F₃)_p have the same definitions as already given, which contains in its molecule two hydantoin rings and two functional groups selected from the group consisting of hydroxyl group, carboxyl group, and ester groups thereof.

Again according to the invention, difunctional hydantoin derivatives similar to the above can be formed by the below-specified embodiment (C), i.e., through the reaction of 1. a bis-glycine derivative of the formula (I-1c) or (I-2c) below,

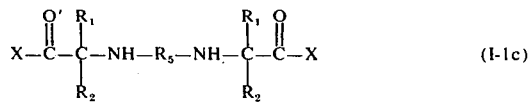

in which
R$_1$, R$_2$, and X have the same significations given as to the formula I-1, and R$_5$ is a divalent organic radical, or

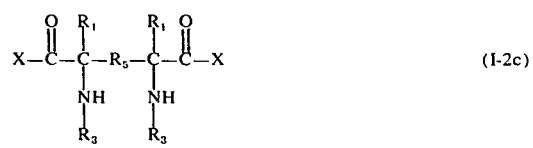

in which
R$_1$, R$_2$, and X have the same significations as those given as to the formula I-2, and
R$_5$ is a divalent organic radical, with 2. a primary diamine of the formula (II-3),

in which $(F_4)_{q'}$ and W have the same significations as already given,
and 3. a diaryl carbonate of the formula (III)

in which $\phi$ and $\phi'$ each denotes a monovalent aromatic group, at such a quantitative ratio that substantially 2 mols of the primary diamine (II-3) is used per mol of the bis-glycine derivative (I-1c) or (I-2c), a compound of the formula (IV-9) or (IV-10) below is formed:

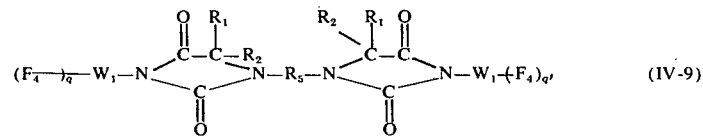

or

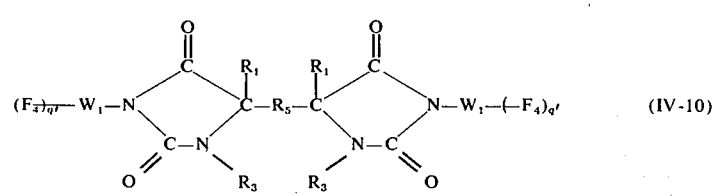

in which
R$_1$, R$_2$, R$_3$, R$_5$, W$_1$, and $(F_4)_{q'}$ have the same definitions as those already given.

The hydantoin derivative of the formula IV-9 or IV-10 also contains in its molecule two hydantoin rings and two functional groups selected from the group consisting of hydroxyl, carboxyl, and ester groups thereof at the two termini, similarly to the hydantoin derivatives of the previously given formulae IV-7 and IV-8.

Because the difunctional derivatives (IV-5, IV-6, IV-7, IV-8, IV-9, and IV-10) formed by the above-described embodiments (A), (B), and (C) possess two functional groups selected from the group consisting of hydroxyl group (—OH), carboxyl group (—COOH), and the ester groups thereof, they serve as the starting materials of substantially linear polymers, such as polyamide, polyester, polyamide-ester, polyimide, polyamide-imide, polycarbonate, polyamide-carbonate, and polyester-carbonate, etc.

It is also possible according to the invention to form polyfunctional hydantoin derivatives containing three or more of the functional groups specified in the foregoing, which can serve as the starting materials of similar polymers of reticulated structure.

The hydantoin derivatives containing two of the afore-specified functional groups formed according to the invention (IV-5, IV-6, IV-7, IV-8, IV-9, and IV-10) are particularly useful as the monomers for making, for example, heat-stable polymers.

It is indeed surprising that the hydantoin ring-forming reaction selectively takes place in the reaction according to the invention, and functional hydantoin derivatives are obtained with high yields, while many other reactions such as formation of urea linkage by the reaction of primary amino group with diaryl carbonate, formation of amide group by the reaction of above-formed urethane group with carboxyl group, formation of aryl ester or carbonate by the reaction of carboxyl group or hydroxyl group with diaryl carbonate, etc. would have been expected.

In the past attempts to synthesize such difunctional hydantoin derivatives as those of the formulae IV-5, IV-6, IV-9, and IV-10 by the method of forming hydantoin rings from iminoacetic acid derivatives and isocyanate, it is essential to first form a special compound of which carboxyl groups are protected with other radicals inert to isocyanate groups, and then effect the reaction of such a compound with isocyanate. Consequently, the protective radicals must be split off from the reaction product by an additional step after the reaction. Thus the method requires cumbersome procedures and is industrially very disadvantageous.

In contrast thereto, according to the process of this invention, industrially readily available and common aminocarboxylic acid can be used. Furthermore, the step for splitting off the protective radicals is unnecessary, but the object difunctional or polyfunctional hydantoin derivatives containing the specified functional groups can be obtained through a single stage reaction. According to the present invention, therefore, a wider varieties of novel difunctional or polyfunctional hydantoin derivatives can be formed with industrial advantage.

Hereinafter several examples of making difunctional hydantoin derivatives in accordance with the typical preferred embodiments of the invention will be given, taking the case of carboxyl group (—COOH) serving as the functional group.

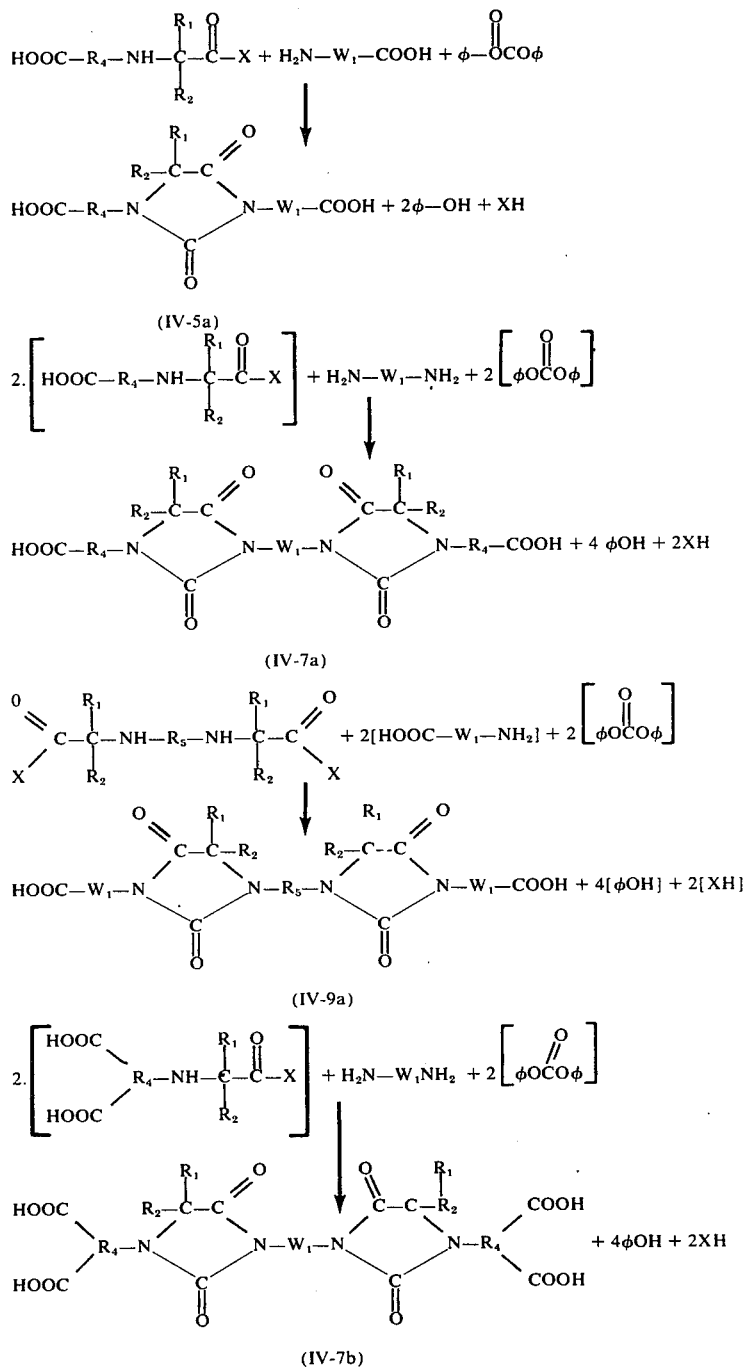

In the reaction formula of above example [4], the two carboxyl groups bonding with $R_4$ are bonded with the two adjacent carbon atoms of $R_4$, respectively.

According to the invention, by any of the embodiments (A), (B), and (C), particularly through the practices illustrated in the foregoing examplary reactions [1] through [4], difunctional hydantoin derivatives containing two esterified carboxyl groups (for example, alkoxycarbonyl or aryloxycarbonyl groups), or two hydroxyl groups (—OH), or a carboxyl group (or an esterified group thereof) and a hydroxyl group; or difunctional hydantoin derivatives containing four carboxyl groups or two anhydride groups thereof, in which each one carboxyl group is bonded with the adjacent two carbon atoms, are formed.

In order to assist the readers' understanding, the reaction will be illustrated by the reaction formula [example 1a], taking the case of the embodiment of [example 1]:

[Example 1a]

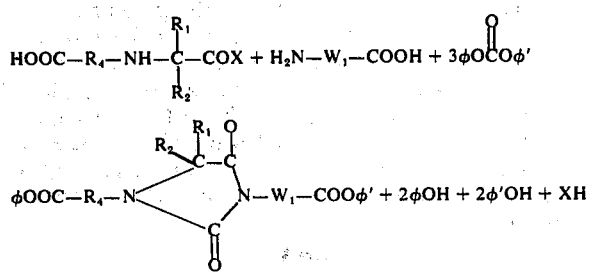

The diaryl carbonates (III) employed in the present invention, particularly diphenyl carbonates, have been industrially produced on large scales as the starting materials of polycarbonates. Because their refining and handling are extremely easier than those of isocyanate, they are advantageously used for the preparation of far wider varieties of polyfunctional hydantoin derivatives containing hydantoin rings, compared with the limited products of the conventional method.

Furthermore, according to our studies, when the diaryl carbonate (III) is used at a quantity exceeding a specific ratio, the carboxyl groups in the formed hydantoin derivatives containing two or more carboxyl groups react with the diaryl carbonate (III) to form an aryl ester. Thus according to the invention, aryl esters of polycarboxylic acids containing hydantoin rings can also be easily obtained.

For example, in the embodiment of example [1] previously given, a dicarboxylic acid diaryl ester containing a hydantoin ring, in which the two carboxyl groups are aryl-esterified can be obtained by using at least 3 molar times the carboxyl-containing glycine derivative of a diaryl carbonate. Similar products containing hydantoin rings can be obtained by the embodiments of examples [2] and [3], by using at least 2 molar times and at least 4 molar times the glycine derivative, respectively, of a diaryl carbonate.

It is likewise possible to form polyaryl esters of polycarboxylic acids containing hydantoin rings, by suitably using excessive quantities of the diaryl carbonate.

The "carboxylate groups" serving as the functional groups of the difunctional hydantoin derivatives of the formulae IV-5, IV-6, IV-7, IV-8, IV-9, and IV-10 formed by the embodiments (A), (B), and (C) already described, therefore also covers the aryl-esterified carboxyl groups formed by the above-mentioned practice.

Generally speaking, the aryl carboxylate exhibits greater reactivity to hydroxyl or amino groups compared with carboxylic acid or alkyl carboxylate. Consequently the aryl esters of polycarboxylic acid containing hydantoin rings formed as above are advantageously utilizable as starting materials of polyester, polyamide, etc.

In the above-mentioned preparation of aryl esters of polycarboxylic acids containing hydantoin rings, the diaryl carbonate is utilized both for the hydantoin ring-forming reaction and aryl ester group-forming reaction with advantage.

The reactions of the invention having been explained above, hereinafter the glycine derivatives (I), amine (II), and diaryl carbonate (III) to be used as the starting components of the reaction, as well as the solvent, catalyst, and reaction conditions employable for the reaction will be explained.

Glycine derivative (I)

The glycine derivatives (I) useful for the invention are the compounds containing at least one glycine residue of the formula G. The typical of such compounds are covered by the already given formulae (I-1) and (I-2).

Still more preferred glycine derivatives are those covered by the formula (I-1d) or (I-2d) below:

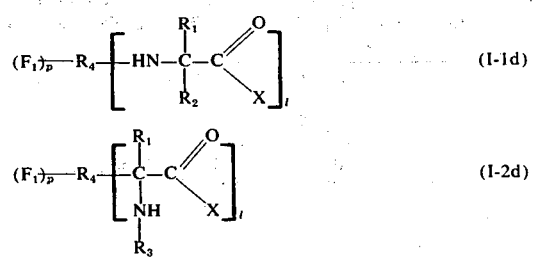

in which $R_1$, $R_2$, $R_3$, $R_4$, $F_1p$, $l$, and X have the same significations as already defined.

As already mentioned, $R_1$, $R_2$, and $R_3$ in the glycine residue constituting the glycine derivatives of the above formula (I-1d) or (I-2d) may be same or different, and each denotes hydrogen atom or a monovalent organic radical. Preferred examples of the monovalent organic radical include aliphatic radicals of 1 to 20 carbons such as methyl, ethyl, propyl, and butyl radicals; alicyclic radicals of 3 to 20 carbons such as cyclohexyl,

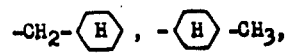

etc.; aromatic radicals of 6 to 20 carbons such as phenyl, benzyl, toluyl, and naphthyl radicals; and organic radicals each containing at least one hetero-element such as oxygen, nitrogen, sulfur, and the like, examples of which including:

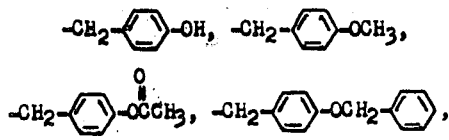

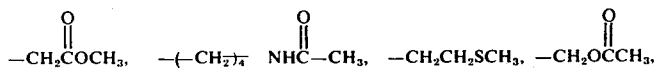

etc. Particularly preferred $R_1$, $R_2$, and $R_3$ are hydrogen atom and methyl, ethyl, phenyl, and benzyl radicals.

The X in the above glycine residue stands for —OA, —SA, —NHA, or —N(A)$_2$ (in which A is hydrogen atom or an organic radical) as previously specified. Suitable organic radicals as A include, for example, aliphatic, alicyclic, and aromatic hydrocarbons, particularly methyl, ethyl, phenyl, and benzyl radicals. Also preferred specific examples of X are —OH, —OCH$_3$, —OC$_2$H$_5$, —SH,

—NH$_2$, —NHCH$_3$, and —N(CH$_3$)$_2$, etc., particularly the radicals of the type —OA.

The $R_4$ forming the glycine derivatives represented by the formula I-1d or I-2d is a $(l+p)$ valent hydrocarbon residue which may contain at least one element selected from the group consisting of oxygen, nitrogen, sulfur, phosphorus and silicon, for example, a saturated or unsaturated hydrocarbon residue of 1 to 20 carbons, which may be aliphatic, alicyclic, aromatic, or heterocyclic. The $l$ plus $p$ bonding hands in the $R_4$ are linked with the carbon atoms.

Specific examples of such hydrocarbon residues forming the $R_4$ in their saturated forms include the following:

i. saturated or unsaturated aliphatic hydrocarbons such as CH$_4$, CH$_3$CH$_3$, CH$_2$ = CH$_2$, CH$_3$.CH$_2$.CH$_3$, CH$_2$ = CH-CH$_3$, CH$_3$CH$_2$CH$_2$CH$_3$, CH$_2$ = CH-CH = CH$_2$, and CH$_3$(CH$_2$)$_4$CH$_3$;

ii. alicyclic hydrocarbons such as

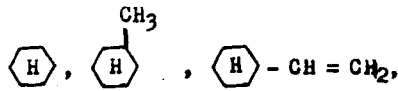

iii. aromatic hydrocarbons such as

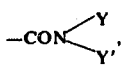

[in which M is a member of the group consisting of -O-, lower alkylenes of 1 - 4 carbons, —NHCO—, —SO—, —CO—,

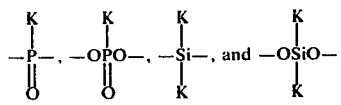

(K standing for a monovalent organic radical)];

iv. heterocyclic compounds such as

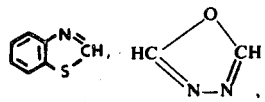

etc.

It should be obvious that the above specific examples are given only by way of illustration, and the scope of this invention is in no way thereby limited.

The hydrocarbon residue ($R_4$) in the above-specified glycine derivatives may be substituted with p substituents ($F_1$).

As already stated, such an $F_1$ is selected from the group consisting of:

halogen atoms (chlorine, bromine, fluorine, iodine) nitro group (—NO$_2$), nitrile group (—CN), tertiary amino group, $$-CON\begin{matrix}Y\\Y'\end{matrix},$$

—OY, —SY, —COY, —OCOY, and —COOY (Y and Y' being either same or different, and each denoting hydrogen atom or a monovalent organic radical).

Examples of monovalent organic radicals which can serve as the Y or Y' in the above include aliphatic, alicyclic, or aromatic hydrocarbon residues of 1 to 20 carbon atoms, the residues optionally containing at least one hetero atom such as oxygen, nitrogen, sulfur, etc.

When $R_4$ is thus substituted with $F_1$, the suitable number of the substituent (p) is not greater than 10, preferably not greater than 5.

Hereinafter some of the specific examples of the glycine derivatives useful for the invention are given, which should never be construed as limitative of the scope of this invention.

a. Monoglycine derivatives:

(a-1) The compounds belonging to the formula (I-1)

H$_2$N—CH$_2$—COOH (glycine)

-continued

H₂N—CH₂—COOCH₃,

H₂N—C(CH₃)(CH₃)—COOC₂H₅

H₂N—CH(C₆H₁₁)—COOH,

H₂N—CH₂—COOC₂H₅,

H₂N—C(C₂H₅)(C₂H₅)—COOC₂H₅

H₂N—CH(CH₂C₆H₅)—COOC₂H₅,

H₂N—CH(CH₂-C₆H₄-OH)—COOC₂H₅,

H₂N—CH(CH₂COCH₃)—COOC₂H₅,

CH₃NHCH₂COOH,

CH₃NHCH₂COS—C₆H₅,

CH₃NHCH₂CON(CH₃)₂,

C₂H₅NHCH₂COOC₂H₅,

CH₃NHCH₂CONH₂,

CH₃NHCH₂CONHCH₃,

C₆H₁₁—NHCH₂COOC₂H₅,

C₆H₅—NHCH₂COOC₂H₅,

C₆H₅—CH₂—NHC(CH₃)(CH₃)—COOC₂H₅, (Br)C₆H₄—CH₂NHCH₂COOCH₃,

NC—C₆H₄—CH₂NHCH₂COOH,

H₃CO—C₆H₄—NHCH₂COOC₂H₅,

HS—C₆H₄—CH₂—NHCH₂COOH,

C₆H₅—CO—O—C₆H₄—NHCH₂COOC₂H₅,

HO—C₆H₄—C(CH₃)(CH₃)—C₆H₄—NHCH₂COOC₂H₅

HO—C₆H₄—O—C₆H₄—NHCH₂COOC₂H₅

HO—(CH₂)—NHCH₂COOH,

HOOC—(CH₂)₂—NHCH₂COOH,

CH₃OOC—C₆H₁₁—NHCH₂COOH,

CH₃—C₆H₄—NHCH₂COOCH₃,

C₆H₅—CH₂—NHCH₂COOC₂H₅, (Cl)C₆H₄—NHCH₂COOH,

NO₂—C₆H₄—NHCH₂COOC₂H₅, (H₃C)(H₃C)N—C₂H₄—NHCH₂COOCH₃,

C₆H₅—O—C₆H₄—NHCH₂COOC₂H₅

C₆H₅—CO—C₆H₄—NHCH₂COOCH₃,

HO—C₆H₄—NHCH₂COOC₂H₅

HO—C₆H₄—CH₂NHCH₂COOC₂H₅, (HO)(HO)C₆H₃—NHCH₂COOC₂H₅

HO—C₆H₁₁—NH₂CH₂COOC₂H₅,

HOOC—(CH₂)₅—NHCH₂COOC₂H₅,

HOOC—C₆H₄—NHCH₂COOCC₂H₅

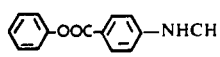 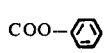 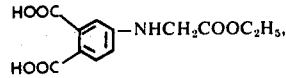
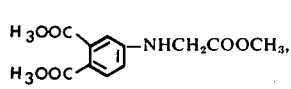 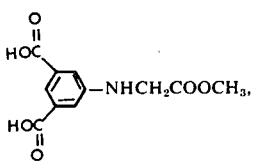
(a-2) The compounds belonging to the formula (I-2)
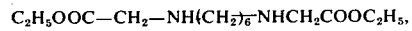
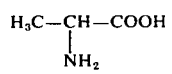 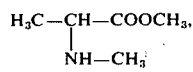
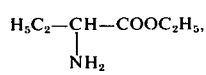 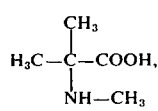
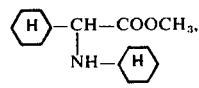 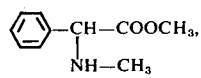
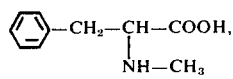 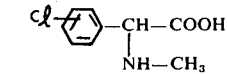
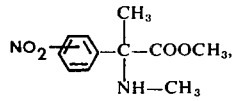 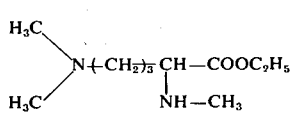
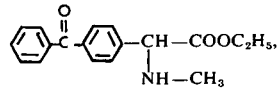 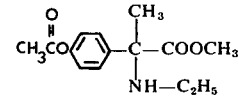
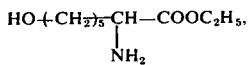 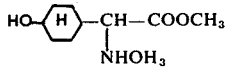
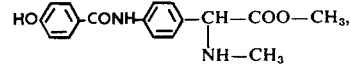 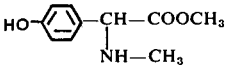
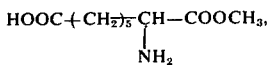 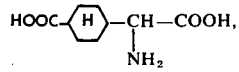
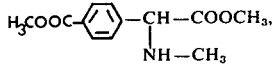 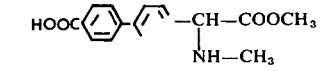
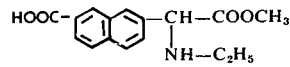 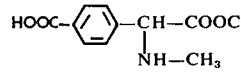
b. Polyglycine derivatives:
(b-1) The compounds belonging to the formula (I-1d)
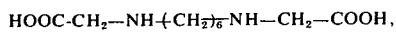
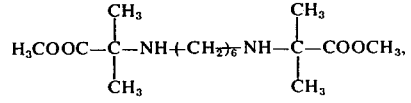
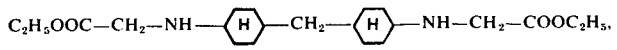

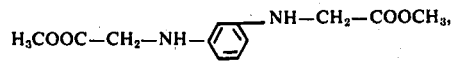
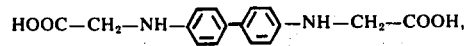
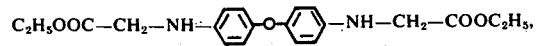
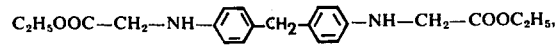
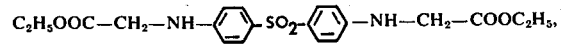
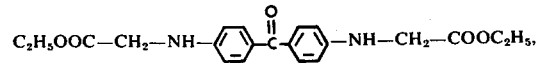
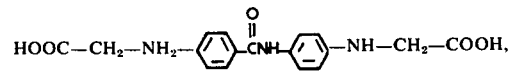
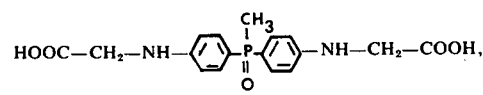
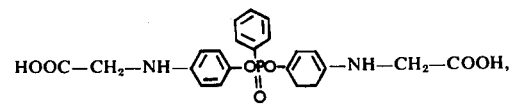
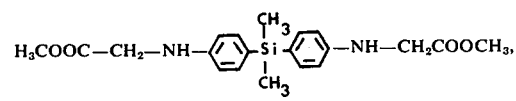
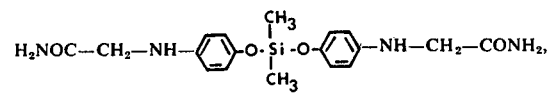
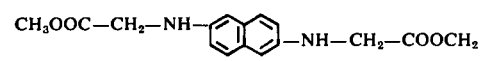
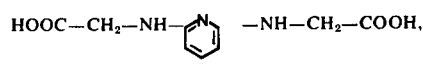
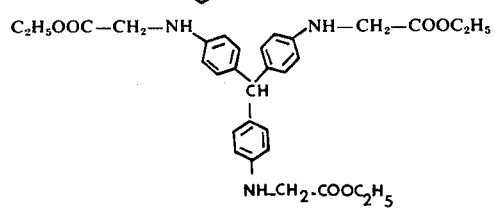

(b-2) The compounds belonging to the formula (I-2d)

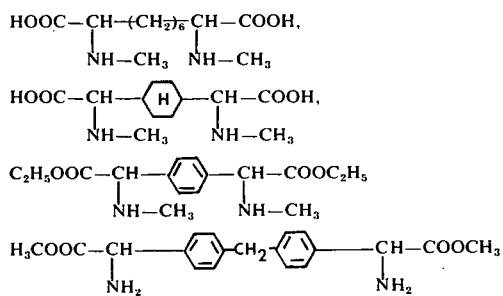

Amines (II)

The amines (II) are the compounds containing at least one primary amino group ($-NH_2$). As aforesaid, ammonia also is covered by this term.

The compounds can be expressed by the formula (II-1) given in the foregoing, which may also be denoted by the formula (II-2) below wherein the W is separated into the skeltal portion $W_1$ and substituent (functional group) portion $F_2$ for better understanding.

$$(F_2)_{q'}W_1(NH_2)_m \qquad (II-2)$$

in which $W_1$, $F_2$, $m$, and $q'$ have the same significations as already defined.

As already stated, $W_1$ is normally an $(m + q)$ valent hydrocarbon residue, for example, a saturated or unsaturated hydrocarbon residue of 1 to 20 carbons which may be aliphatic, alicyclic, aromatic or heterocyclic and optionally contains at least a member of the group consisting of oxygen, nitrogen, sulfur, phosphorus and silicon.

Specific examples of such $W_1$ perfectly correspond with those of the $R_4$ of the glycine derivatives (I).

Such $W_1$ may be substituted with $q'$ substituents ($F_2$). Examples of $F_2$ again perfectly correspond with those of $F_1$.

In the selection of amine (II) according to the foregoing explanations, it is furthermore desirable to follow the conditions given below. To wit, when $m + q \geqq 2$, a compound in which the primary amino group ($-NH_2$) and the carboxyl group expressed by the formulae $-COOY$, 

etc. and/or the functional derivatives thereof are bonded with same carbon atom, i.e., a compound covered by the definition of glycine derivatives (I) already given, is outside the scope of amine (II).

Again, if the $-NH_2$, $-OY$, or $-SY$ radicals are bonded with each the carbon atom adjacent thereto, generally intramolecular ring closure through the reaction of such an amine with diaryl carbonate takes place before the hydantoin ring-forming reaction, to form cyclic compounds such as ethyleneureas, oxazolidone, or ethylene carbonates. Therefore, such amine compounds should be avoided.

Furthermore, even when the aforesaid radicals are bonded with the carbon atoms spaced by no less than 3 atoms, still the use of such an amine which is apt to form intramolecular cyclic compounds such as 1,8-naphthylenediamine, is unsuitable for the purpose of this invention.

Hereinafter preferred examples of specific amines (II) will be given.

i. When $m = 1$ and $q = 0$:

| | |
|---|---|
| $NH_3$ | Ammonia |
| $C_2H_5-NH_2$ | Ethylamine |
| $C_4H_9-NH_2$ | Butylamine |
| $CH=CH-CH_2-NH_2$ | Allylamine |
| 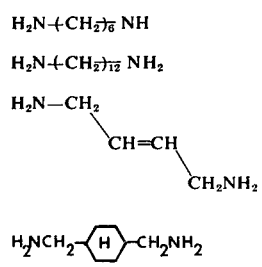 Cyclohexylamine | |

| | |
|---|---|
| Benzylamine | |
| Aniline | |
| α-Naphthylamine | |
| 3-Amino pyridine | | ii. When $m \geqq 2$ and $q = 0$:

| | |
|---|---|
| $H_2N+CH_2)_6 NH_2$ | Hexamethylenediamine |
| $H_2N+CH_2)_{12} NH_2$ | Dodecamethylenediamine |
| $H_2N-CH_2$<br>　　　　$CH=CH$<br>　　　　　　　$CH_2NH_2$ | 1,4-Diamino-trans-butene (2) |
| $H_2NCH_2$-(H)-$CH_2NH_2$ | Cyclohexane-1,4-bis(methylene amine) |

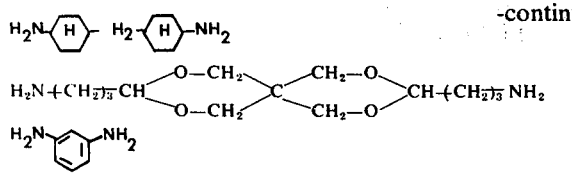
4,4'-Methylene-bis-cyclohexylamine
3,9-bis(3-aminopropyl)-2,4,8,10-tetraoxaspiro(5,5)undecane
m-Phenylenediamine

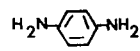
p-Phenylenediamine

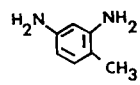
2,4-toluylenediamine

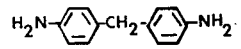
4,4'-Methylenedianiline

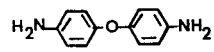
4,4'-Oxydianiline

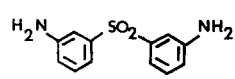
3,3'-Sulfonyldianiline

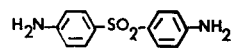
4,4'-Sulfonyldianiline

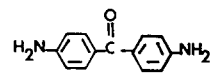
4,4'-Diaminobenzophenone

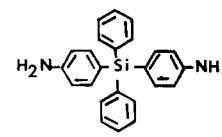
4,4'-Diaminotetraphenylsilane

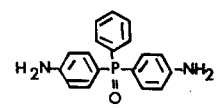
4,4'-Diaminotriphenylphosphineoxide

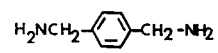
p-Xylylenediamine

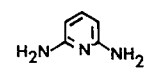
2,6-Diaminopyridine

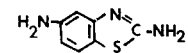
2,5-Diaminobenzothiazole

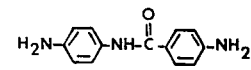
4,4'-Diaminobenzanilide

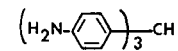
Tris(4-aminophenyl)methane

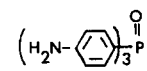
Tris(4-aminophenyl)phosphine oxide

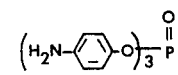
Tris(4-aminophenyl)phosphite

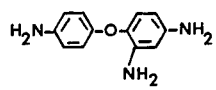 2,4,4'-Triaminodiphenylether
iii. When $m=1$, and $q \geq 1$:
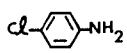 p-Chloroaniline
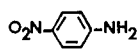 p-Nitroaniline
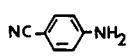 p-Cyanoaniline
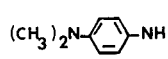 p-(Dimethylamino)aniline
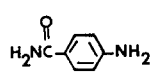 p-Aminobenzamide
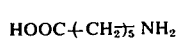 ε-Aminocaproic acid
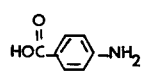 p-Aminobenzoic acid
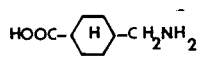 4-Aminomethylcyclohexane carboxylic acid
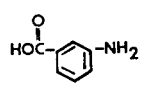 m-Aminobenzoic acid
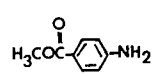 Methyl p-aminobenzoate
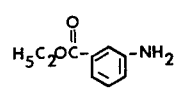 Ethyl m-aminobenzoate
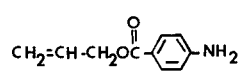 Allyl p-aminobenzoate
 p-Aminophenol
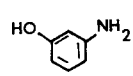 m-Aminophenol

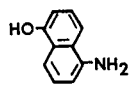 5-Amino-β-naphthol
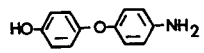 4-Amino-4'-hydroxy-diphenylether
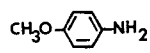 4-Aminoanithol
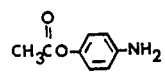 4-Aminophenyl acetate
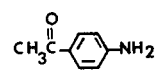 4-Amino acetophenone
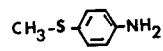 (4-Aminophenyl)-methylthioether
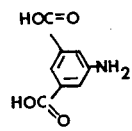 5-Aminoisophthalic acid
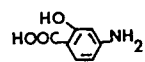 O-Hgdroxy-p-aminobenzoic acid
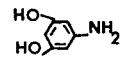 3,5-Dihydroxyaniline
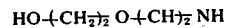 Diglycolamine
iv. When $m \geqq 2$, and $q \geqq 1$:
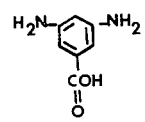 3,5-Diaminobenzoic acid

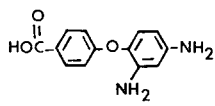
4-(2,4-Diaminophenyloxy)benzoic acid

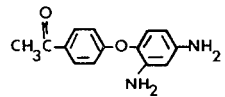
4-(2,4-Diaminophenyloxy)acetophenone

The above-described glycine derivatives (I) and amines (II) may be used in the reaction in the form of their ammonium salts, e.g., carbonate, hydrochloride, sulfate, phosphate, sulfonate, etc. In such a case, excepting, for example, carbonate which easily dissociates under heating, it is necessary to separately use an acid acceptor such as a tertiary amine to secure regeneration of amino groups at the time of the reaction.

Again, if the compounds (I) and (II) contain carboxyl groups and phenolic hydroxyl groups, a part or whole of such compounds may be used for the reaction in the form of carboxylate, phenolate, or the like, of tertiary amine salt, alkali metal salt, etc.

Diaryl carbonate (III)

In the diaryl carbonate (III) to be employed in the present invention, $\phi$ and $\phi'$ are same or different monovalent aromatic radicals. While they are subject to no other requirement, because the radicals become $\phi$OH or $\phi'$OH after the reaction and do not enter into the reaction product, preferably the compounds have low molecular weights, and are stable as diaryl carbonate, $\phi$OH, or $\phi'$OH. Generally the diaryl carbonates containing $\phi$ and $\phi'$ which are strongly acidic in the form of $\phi$OH and $\phi'$OH show higher reactivity. Utilizing this phenomenon it is possible to select diaryl carbonate of particularly high activity depending on the type of the compounds (I) and (II) to be used.

Generally the preferred diaryl carbonates include diphenyl carbonate, dicresyl carbonate, phenylcresyl carbonate, bis(nitrophenyl) carbonate, bis(chlorophenyl)carbonate, dinaphthyl carbonate, and dibiphenyl carbonate. Particularly diphenyl carbonate is cheap and normally used with the best preference.

According to the invention, the diaryl carbonate is primarily used in stoichiometric quantities or somewhat in excess with advantage. However, when the diaryl carbonate-decomposing reaction or other side-reactions are apt to occur depending on the specific reaction conditions, the diaryl carbonate is preferably used in the quantity as will off-set its expected loss through such side-reactions.

Solvent:

According to the subject process, under normal reaction conditions the diaryl carbonate is liquid, and consequently serves also as the solvent. Also, the phenols side-produced with the progress of the reaction are in most cases good solvents for the starting glycine derivative (I) amine (II), intermediate products and the other product (IV). Therefore in many cases the reaction can be performed without special addition of reaction solvent.

It is possible, however, to assist smoother progress of the reaction, by the addition of a reaction solvent.

A preferred solvent should be substantially inert to the reaction in accordance with the subject process, have a boiling point not lower than 100°C., more preferably not lower than 150°C., and show high dissolving action of the starting materials as well as the intermediate products.

Specific examples of such solvents include aprotic polar solvents such as N-methylpyrrolidone, tetramethylenesulfone, dimethylacetamide, dimethylformamide, nitrobenzene, and the like. Phenolic solvents such as cresol, phenol, xylenol, etc., can also be used with favorable results.

The quantity of such a solvent to be added is not critical. It is not always necessary to use the solvent at a constant concentration throughout the reaction, but the concentration can be suitably adjusted by such procedures as condensing, dilution, etc.

Catalyst:

The reaction of the invention normally smoothly progresses to produce the object product, without the assistance of special catalyst. If necessary, however, suitable catalyst may be used for accelerating the reaction.

Examples of useful catalyst include oxides, hydroxides, alcoholates, chlorides, and organic compounds of such metals as alkali metals, alkaline earth metals, tin, titanium, antimony, and aluminium; tertiary amines, and quaternary ammonium base, etc. As more specific examples, calcium oxide, magnesium oxide, lithium hydroxide, sodium hydroxide, calcium hydroxide, sodium ethylate, triethylamine, triethylammonium hydroxide, butyl titanate, magnesium chloride, and dibutyltindi-laurate may be named. Such a catalyst is normally used within the range of approximately 0.05 – 2 mol% to the starting materials.

Reaction conditions, separation and refining of the product;

Hereinafter the generally employable reaction conditions for the subject process will be explained.

The present invention is practiced by the reaction of already specified glycine derivative (I), amine (II), and diaryl carbonate (III), if necessary, in the presence of solvent and catalyst, under heating.

Suitable reaction temperatures are within the range of 100° – 300°C., preferably from 130° – 270°C. The reaction time varies depending on other reaction conditions, but normally desirable range is from 0.5 to 30 hours. Obviously, this range is not critical, and shorter or longer reaction time may be employed. It is preferred, however, that the temperature should be gradually raised to inhibit undesirable sidereactions.

The reaction is normally effected under normal pressure, while distilling off the side-produced XH (for example, if X is —OH, water, if X is —OCH$_3$, methanol, and when X is —OC$_2$H$_5$, ethanol, etc.). If necessary, it is also possible to advance the reaction while distilling off the by-produced $\phi$OH, $\phi'$OH, or a part of the solvent. Furthermore, if necessary a reflux condenser may be connected with the reactor to effect the reaction while refluxing the solvent, $\phi$OH, $\phi'$OH, etc. In such a practice, the reflux condenser may be of a fractionation type to allow the removal by distillation of low temperature-boiling XH alone.

The reaction can be effected in air, but because the compounds generally sensitive to oxidation such as the glycine derivatives, amine, phenol, etc. are used as the reactants, it is preferred to use an inert atmosphere such as of nitrogen, argon, etc.

When ammonia or low temperature-boiling amines or glycine derivatives are used, the reaction is preferably performed in closed system to prevent the volatilization of such reactants. In the closed system, in certain cases the reaction system is placed under elevated pressures.

It is also permissible to use such low boiling point reactants in open system at normal pressure, by effecting the reaction by passing the low boiling point reactants in vapor form through the reaction system.

Thus formed hydantoin derivatives (IV) can be separated from the reaction mixture, for example, by solidification of the product after distilling off the side-products, solvent, etc., reprecipitation from a non-solvent of the product, or by combination of such means.

The object product so separated can be further refined by the means known per se, such as recrystallization, distillation or chromatography.

The structure of each hydantoin derivatives obtained according to the invention can be confirmed again by the means known per se, such as melting point measurement, infrared absorption spectrum, nuclear magnetic resonance, and elementary analysis. Also the purity of the product can be determined by various chromatographies.

As so far described in the foregoing, according to the invention very broad and versatile classes of hydantoin derivatives can be obtained without using isocyanates, through single-stage reaction with high yield. Because no isocyanate is used, it becomes unnecessary to convert amine to the isocyanate in each run, but the amine can be reacted as it is, with the relatively stable diaryl carbonate. Consequently, it is possible according to the invention to form a wide variety of hydantoin derivatives with relatively simple equipments compared with the process using isocyanates. Furthermore, hydantoin derivatives containing the functional groups easily reactable with isocyanate, such as carboxyl or hydroxyl radicals, can be directly produced without the cumbersome procedures of advance protection of such functional groups and later splitting off of the protective groups.

The hydantoin derivatives produced according to the invention are directly useful as pesticides, medicines, or as their intermediates. They may also be further processed, for example, reacted with various aldehydes and then hydrolyzed to form various -amino acids.

As already mentioned, the invention also allows easy preparation of hydantoin derivatives containing one or plural functional groups such as carboxyl, carboxylic acid anhydride or two carboxyl groups convertible thereto, esterified carboxyl, particularly aryl-esterified carboxyl groups of high reactivity and hydroxyl group (-OH). Therefore, using, for example, difunctional hydantoin derivatives among such products, various linear polymers can be prepared either directly or through reactions thereof with other diamines, aminocarboxylic acid, hydroxy carboxylic acid, dihydric alcohol, hydroxylamine, or other difunctional compounds such as diallyl carbonate, phosgene, etc. Again from trifunctional hydantoin derivatives, polymers of reticulated structure can be obtained by similar means.

EXAMPLE 1

14.0 Grams (0.1 mol) of glycine ethyl ester hydrochloride, 4.8 g (0.05 mol) of ammonium carbonate, and 21.4 g (0.1 mol) of diphenyl carbonate were added into 25 ml of N-methylpyrrolidone, and the system was gradually heated until its temperature reach 180°C., in nitrogen current under stirring. The system was further heated for 2 hours at 180°C., then allowed to cool off to 120°C., added with 9.3 g (0.1 mol) of aniline, and again reacted under heating at 180°C. for 6 hours. Thereafter the reaction mixture was filtered to be removed of the ammonium chloride formed. The filtrate was concentrated, and the residue was recrystallized from a minor amount of methanol to provide 13.2 g (75% yield) of white, needle-like crystal having the melting point at 149.0° – 149.5°C. The infrared absorption spectrum of the product indicated the formation of 3-phenyl hydantoin, by NH stretching vibration at 2800 – 3500 $cm^{-1}$, and the absorptions characteristic to hydantoin at 1760 $cm^{-1}$ and 1710 $cm^{-1}$. The elementary analysis values of the product were: C, 61.12%; H, 4.73%; and N, 15.70%; which well corresponded to the theoretical values of C, 61.36%; H, 4.58%; and N, 15.90%.

EXAMPLE 2

8.95 Grams (0.05 mol) of N-phenylglycine ethyl ester, 10.7 g (0.05 mol) of diphenyl carbonate, and 3.7 g (0.05 mol) of n-butylamine were dissolved in 30 ml of N-methylpyrrolidone, and the solution was gradually heated to 190°C. in nitrogen current under stirring. The system was allowed to further react at 190°C. for 8 hours, and thereafter the side-produced ethanol, phenol, and N-methylpyrrolidone which served as the solvent, were distilled off from the reaction mixture. A minor amount of methanol was added to the distillation residue to effect recrystallization of the preoduct, and thus 9.0 g (78% yield) of white, platy crystal was obtained. The product had a melting point of 75.0° – 75.5°C., and its infrared absorption spectrum indicated the formation of 1-phenyl-3-n-butylhydantoin by the absorptions characteristic to hydantoin at 1755 $cm^{-1}$ and 1700 $cm^{-1}$. The elementary analysis values were as follows:

Elementary analysis values:

| | C | H | N |
|---|---|---|---|
| Found: | 67.53% | 6.72% | 12.32% |
| Calculated: | 67.22% | 6.94% | 12.06% |

EXAMPLE 3

19.3 Grams (0.1 mol) of phenylalanine, 21.4 g (0.1 mol) of diphenyl carbonate, and 9.3 g (0.1 mol) of aniline were dissolved in 50 ml of N-methylpyrrolidone, and the solution was gradually heated to 190°C. in nitrogen current under stirring. The system was further allowed to react at 190°C. for 5 hours, and thereafter the by-produced ethanol, phenol, and N-methylpyrrolidone which served as the solvent were distilled off.

Dissolving the residue in a minor amount of methanol and cooling the solution, flaky crystal was precipitated. By recovering the crystal by filtration and drying the same, 18.3 g (70% yield) of 3-phenyl -5-benzylhydantoin was obtained. The infrared absorption spectrum of the product indicated the NH stretching vibration at 2800 – 3500 cm$^{-1}$, and absorptions characteristic to hydantoin at 1810 cm$^{-1}$, 1760 cm$^{-1}$, and 1700 cm$^{-1}$. The elementary analysis values were as follows:

Elementary analysis values:

| | C | H | N |
|---|---|---|---|
| Found: | 72.10% | 5.53% | 10.38% |
| Calculated: | 72.16% | 5.30% | 10.52% |

EXAMPLE 4

10.3 Grams (0.1 mol) of glycine ethyl ester, 21.4 g (0.1 mol) of diphenyl carbonate, and 6.8 g (0.4 mol) of ammonia were dissolved in 30 ml of N-methylpyrrolidone, and the system was gradually heated in an autoclave to 180°C. The system was thus allowed to react at 180°C. for 8 hours, and thereafter the excessive ammonia, by-produced ethanol and phenol, and N-methylpyrrolidone were distilled off. Recrystallizing the residue from methanol, 8.2 g (82% yield) of needle-like crystal of hydantoin was obtained, which had a melting point of 219°C., well corresponding to the known melting point of hydantoin which is 220°C.

EXAMPLES 5 – 23

Various hydantoin derivatives (IV) were formed, using various glycine derivatives (I), amines (II), and diaryl carbonates (III) of various quantities. The types and quantities of the starting materials, and the structures of the products (IV) were as given below. Also the reaction conditions, yields, melting points and elementary analysis values, as well as characteristic absorptions in infrared analysis, of the products are given in Table 1.

Example 5

(I) 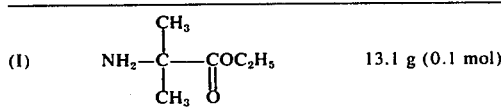  13.1 g (0.1 mol)

(II) NH$_3$ (ammonia)  3.4 g (0.2 mol)

(III)   21.4 g (0.1 mol)

(IV) 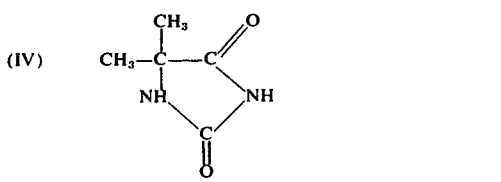

Example 6

(I) CH$_3$NHCH$_2$COH  4.45 g (0.05 mol)
      ‖
      O (II)   4.65 g (0.05 mol)

(III)   10.7 g (0.05 mol)

Example 6-continued (IV) 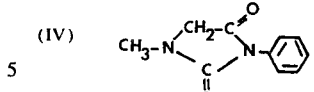

Example 7

(I) CH$_3$NHCH$_2$CS- 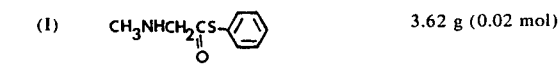  3.62 g (0.02 mol)

(II)   1.86 g (0.02 mol)

(III)   4.28 g (0.02 mol)

(IV) 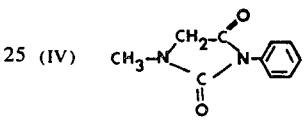

Example 8

(I) CH$_3$NHCH$_2$CNHCH$_3$  2.04 g (0.02 mol)
      ‖
      O (II)   1.86 g (0.02 mol)

(III)   4.28 g (0.02 mol)

(IV) 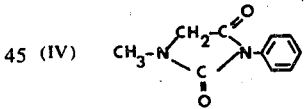

Example 9

(I) CH$_3$NHCH$_2$CN(CH$_3$)$_2$  2.32 g (0.02 mol)

(II)   1.86 g (0.02 mol)

(III)   4.28 g (0.02 mol)

(IV) 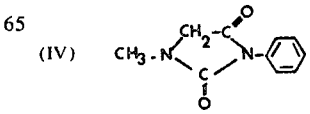

Example 10

| | | |
|---|---|---|
| (I) | Ph-NH-CH$_2$COC$_2$H$_5$ (C=O) | 17.9 g (0.1 mol) |
| (II) | Ph-NH$_2$ | 9.3 g (0.1 mol) |
| (III) | Ph-O-C(=O)-O-Ph | 21.4 g (0.1 mol) |
| (IV) | Ph-N(CH$_2$-C(=O))-C(=O)-N-Ph (hydantoin ring) | |

Example 11

| | | |
|---|---|---|
| (I) | Ph-NH-CH$_2$-C(=O)-NH$_2$ | 15.0 g (0.1 mol) |
| (II) | Ph-NH$_2$ | 9.3 g (0.1 mol) |
| (III) | Ph-O-C(=O)-O-Ph | 21.4 g (0.1 mol) |
| (IV) | Ph-N(CH$_2$-C(=O))-C(=O)-N-Ph | |

Example 12

| | | |
|---|---|---|
| (I) | Ph-NH-CH$_2$COC$_2$H$_5$ (C=O) | 5.37 g (0.03 mol) |
| (II) | CH$_3$C(=O)-C$_6$H$_4$-NH$_2$ | 4.05 g (0.03 mol) |
| (III) | Ph-O-C(=O)-O-Ph | 6.42 g (0.03 mol) |
| (IV) | Ph-N(CH$_2$-C(=O))-C(=O)-N-C$_6$H$_4$-CCH$_3$(=O) | |

Example 13

| | | |
|---|---|---|
| (I) | Ph-NHCH$_2$COC$_2$H$_5$ (C=O) | 1.8 g (0.01 mol) |
| (II) | CH$_3$O-C$_6$H$_4$-NH$_2$ | 1.2 g (0.01 mol) |
| (III) | Ph-O-C(=O)-O-Ph | 2.2 g (0.01 mol) |
| (IV) | Ph-N(CH$_2$-C(=O))-C(=O)-N-C$_6$H$_4$-OCH$_3$ | |

Example 14
| | | |
|---|---|---|
| (I) | 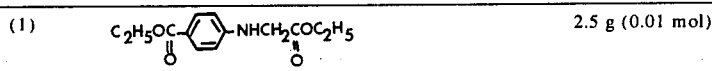 | 2.5 g (0.01 mol) |
| (II) |  | 0.93 g (0.01 mol) |
| (III) |  | 2.14 g (0.01 mol) |
| (IV) | 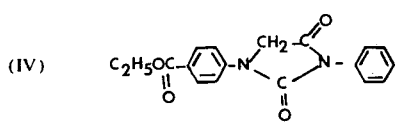 | |
Example 15
| | | |
|---|---|---|
| (I) | 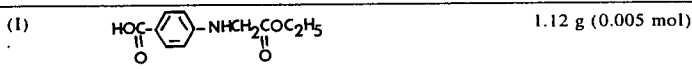 | 1.12 g (0.005 mol) |
| (II) |  | 0.64 g (0.005 mol) |
| (III) |  | 1.07 g (0.005 mol) |
| (IV) | 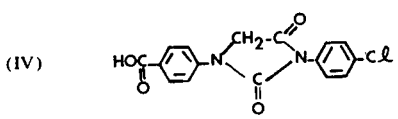 | |
Example 16
| | | |
|---|---|---|
| (I) | 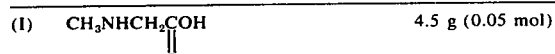 | 4.5 g (0.05 mol) |
| (II) |  | 3.7 g (0.05 mol) |
| (III) |  | 10.7 g (0.05 mol) |
| (IV) | 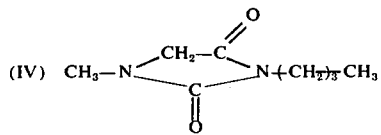 | |
Example 17
| | | |
|---|---|---|
| (I) | 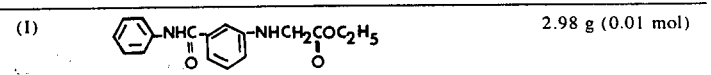 | 2.98 g (0.01 mol) |
| (II) |  | 0.93 g (0.01 mol) |
| (III) |  | 2.14 g (0.01 mol) |

Example 17-continued
(IV) 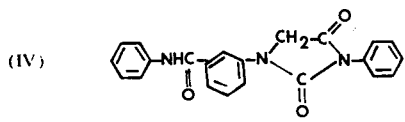
Example 18
| (I) | 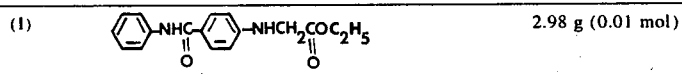 | 2.98 g (0.01 mol) |
|---|---|---|
| (II) |  | 0.93 g (0.01 mol) |
| (III) |  | 2.14 g (0.01 mol) |
| (IV) | 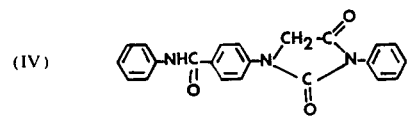 | |
Example 19
| (I) | 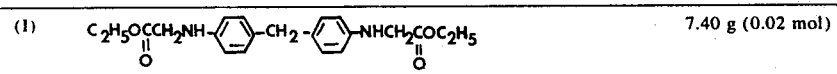 | 7.40 g (0.02 mol) |
|---|---|---|
| (II) |  | 6.0 g (0.04 mol) |
| (III) |  | 8.6 g (0.04 mol) |
| (IV) | 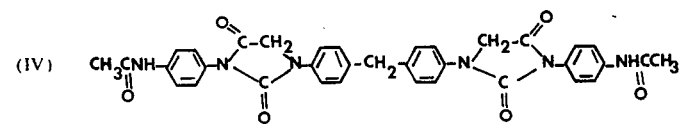 | |
Example 20
| (I) |  | 3.58 g (0.02 mol) |
|---|---|---|
| (II) |  | 3.30 g (0.02 mol) |

Example 20-continued
| | | |
|---|---|---|
| (III) |  | 4.28 g (0.02 mol) |
| (IV) | 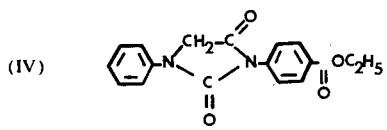 | |
Example 21
| | | |
|---|---|---|
| (I) | 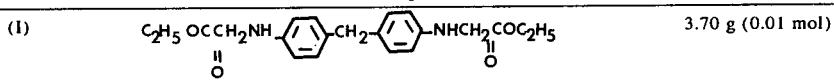 | 3.70 g (0.01 mol) |
| (II) |  | 1.86 g (0.02 mol) |
| (III) |  | 4.28 g (0.02 mol) |
| (IV) | 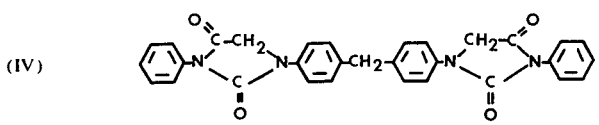 | |
Example 22
| | | |
|---|---|---|
| (I) | 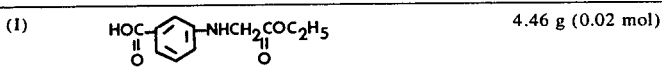 | 4.46 g (0.02 mol) |
| (II) |  | 2.76 g (0.02 mol) |
| (III) |  | 4.28 g (0.02 mol) |
| (IV) | 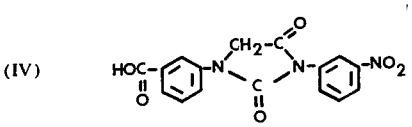 | |
Example 23
| | | |
|---|---|---|
| (I) | 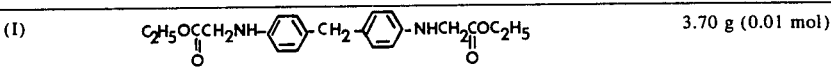 | 3.70 g (0.01 mol) |
| (II) |  | 2.76 g (0.02 mol) |

Example 23-continued (III) 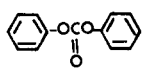  4.28 g (0.02 mol)

(IV) 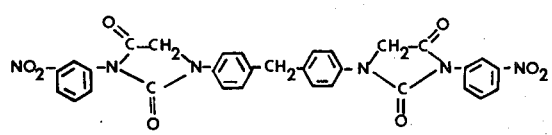

Table 1

| Ex. No. | Solvent (ml) | Reaction Temp. Reaction Time (°C./hr.) | Yield (%) | Melting Point (°C.) | Wavelengths of Characteristics Absorptions (cm$^{-1}$) | | Elementary Analysis Values (%) | | | |
|---|---|---|---|---|---|---|---|---|---|---|
| | | | | | | | C | H | N | S |
| 5 | N-methyl-pyrrolidone (30) | 180/8 (in autoclave) | 13 | 174.5 -175.0 | 2600 - 3500 (NH) 1765, 1720, 1690 (hydantoin) | Calcd. Found | — | | — | |
| 6 | Cresol (10) | 200/5 | 55 | 94–95 | 1810, 1780, 1720 (hydantoin) | Calcd. Found | 63.15 63.43 | 5.30 5.15 | 14.73 14.95 | — |
| 7 | Cresol (10) | 170/15 | 89 | 94.5 -95 | do. | Calcd. Found | — | | | |
| 8 | Cresol (10) | 240/20 | 21 | 90–93 | do. | Calcd. Found | — | | | |
| 9 | Cresol (10) | 240/20 | 26 | 90–93 | do. | Calcd. Found | — | | | |
| 10 | Cresol (100) | 200/5 | 92 | 137.5 -138 | 1765, 1715 (hydantoin) | Calcd. Found | 71.41 71.62 | 4.80 4.92 | 11.11 11.22 | — |
| 11 | Cresol (100) | 240/25 | 26 | 136–138 | do. | Calcd. Found | — | | | |
| 12 | Cresol (10) | 200/7 | 77 | 273–274 | 1780, 1715 (hydantoin) 1680 (ketone) | Calcd. Found | 69.40 69.72 | 4.80 4.99 | 9.52 9.32 | — |
| 13 | Cresol (3) | 200/3 | 71 | 144–145 | 1770, 1710 (hydantoin) 1240 (ether) | Calcd. Found | 68.07 67.76 | 4.99 4.68 | 9.93 9.68 | — |
| 14 | Cresol (10) | 180/10 | 63 | 191–192 | 1780, 1710 (hydantoin) 1720 ($\nu$C=O, ester) | Calcd. Found | 66.65 66.73 | 4.97 4.96 | 8.64 8.32 | — |
| 15 | Cresol (5) | 200/3 | 25 | 300< | 2600-3500, 1680 (COOH) 1780, 1720 (hydantoin) | Calcd. Found | 58.10 58.32 | 3.35 3.15 | 8.47 8.76 | 10.72 10.43 |
| 16 | Cresol (10) | 200/10 | 41 | boiling point 90°C/1mmHg | 1770/1710 (hydantoin) | Calcd. Found | 56.45 56.56 | 8.29 8.19 | 16.46 16.32 | — |
| 17 | Cresol (10) | 190/10 | 69 | 225–226 | 3300, 1655 (amide) 1780, 1725 (hydantoin) | Calcd. Found | 71.15 71.28 | 4.61 4.82 | 11.32 11.15 | — |
| 18 | Cresol (10) | 190/10 | 73 | 258–260 | 3340, 1650 (amide) 1775, 1720 (hydantoin) | Calcd. Found | 71.15 71.16 | 4.61 4.91 | 11.32 11.21 | — |
| 19 | Cresol (30) | 200/2 | 48 | 295 | 3300, 1660 (amide) 1770, 1710 (hydantoin) | Calcd. Found | 66.65 66.87 | 4.80 4.61 | 13.33 13.72 | — |
| 20 | Cresol (10) | 200/3 | 66 | 184–5 | 1780, 1710 (hydantoin) 1720 (ester) | Calcd. Found | 66.65 66.82 | 4.97 4.63 | 8.64 8.92 | — |
| 21 | Cresol (15) | 160/25 | 53 | 225–6 | 1770, 1715 (hydantoin) | Calcd. Found | 72.08 72.23 | 4.68 4.76 | 10.85 10.87 | — |
| 22 | Cresol (10) | 200/7 | 45 | 245–6 | 2300-3700, 1700 (COOH) 1780, 1730 (hydantoin) | Calcd. Found | 56.31 56.58 | 3.25 3.58 | 12.31 12.37 | — |
| 23 | Cresol (10) | 220/5 | 74 | 135–6 | 1775, 1720 (hydantoin) | Calcd. Found | 61.38 61.45 | 3.66 3.32 | 13.86 13.79 | — |

EXAMPLE 24

8.92 Grams (0.04 mol) of m-ethoxycarbonyl methylaminobenzoic acid, 3.96 g (0.02 mol) of 4,4'-diaminodiphenylmethane, and 8.56 g (0.04 mol) of diphenyl carbonate were added to 50 ml of N-methylpyrrolidone, and the formed solution was gradually heated under stirring in nitrogen current. The bath temperature reached 200°C. after approximately 2 hours of the heating. The system was allowed to react at 200°C. for the subsequent 5 hours. After the reaction, the phenol formed and N-methylpyrrolidone served as the solvent were distilled off under nitrogen current until a crystalline product started to precipitate, while the bath temperature was maintained at 200°C. The remaining system was cooled off to room temperature, and allowed to stand until the crystalline product was precipitated and the system was solidified. The crystal was recovered by filtration, washed with methanol, and dried to provide 11.2 g (93% yield) of a crystal melting at 264°C. The infrared spectrum of the product showed the absorption of carboxylic acid at 2500 - 3500 cm$^{-1}$, and also the absorptions characteristic to stretching vibration of hydantoin carbonyl at 1780 cm$^{-1}$ and 1720 cm$^{-1}$. The absorption by carboxylic acid in the vicinity of 1770 1700 $^{-1}$ overlapped with that of the hydantoin at 1720 cm$^{-1}$ and was recognizable as a shoulder.

The acid value of the product was 184 (theoretical value being 186), and the results of elementary analysis well corresponded with the theoretical values as below:

Elementary analysis values;

| | C | H | N |
|---|---|---|---|
| Found: | 65.42% | 3.78% | 9.12% |
| Calculated: | 65.56% | 4.00% | 9.27% |

EXAMPLE 25

8.92 Grams (0.04 mol) of p-ethoxycarbonyl methylaminobenzoic acid, 3.96 g (0.02 mol) of 4,4'-diaminodiphenylmethane, and 9.68 g (0.04 mol) of dicresyl carbonate were added to 50 ml of N-methyl pyrrolidone, and the mixture was gradually heated under stirring in nitrogen gaseous current. The bath temperature reached 200°C. after approximately 2 hours of the heating. The system was further allowed to react at 200°C. for 7 hours. Thereafter the formed cresol, and N-methylpyrrolidone served as the solvent were distilled off until a crystalline product started to precipitate, in nitrogen current, while the bath temperature was maintained at 200°C. The system was allowed to cool off to room temperature and stand. Whereupon the crystalline product was precipitated, and the system was solidified. The crystal was recovered by filtration, washed with methanol, and dried to provide 9.8 g (81% yield) of the crystalline product which was not melted up to 300°C. The infrared spectrum of the product showed the absorption of carboxylic acid at 2500 – 3500 $cm^{-1}$, that of hydantoin at 1780 $cm^{-1}$ and 1730 $cm^{-1}$, and that of carboxyl group at 1690 $cm^{-1}$. The elementary analysis values well corresponded with the theoretical values as follows:

Elementary analysis values:

| | C | H | N |
|---|---|---|---|
| Found: | 65.38% | 4.13% | 9.18% |
| Calculated: | 65.56% | 4.00% | 9.27% |

EXAMPLE 26

11.1 Grams (0.03 mol) of ethyl diphenylmethane-4,4'-diiminoacetate, 8.22 g (0.06 mol) of m-aminobenzoic acid, and 12.8 g (0.06 mol) of diphenyl carbonate were added to 70 ml of N-methylpyrrolidone, and the system was gradually heated under stirring in the atmosphere of nitrogen current. The bath temperature reached 200°C. after approximately 2 hours, and at said temperature the system was reacted for additional 7 hours. Then the phenol formed and N-methylpyrrolidone served as the solvent were distilled off in the nitrogen current until a crystalline precipitate started to be formed, while maintaining the bath temperature at 200°C. The system was allowed to cool off to room temperature, and solidified during the subsequent standing. The crystal was recovered by filtration, washed with methanol, and dried to provide 14.0 g (78% yield) of a crystalline product which was not melted up to 300°C. The infrared spectrum of the product showed the absorption by carboxylic acid at 2300 – 3500 $cm^{-1}$, that of hydantoin bond at 1770 $cm^{-1}$ and 1720 $cm^{-1}$, and that from the C=O stretching vibration of carboxylic acid at 1675 $cm^{-1}$. The found values of elementary analysis well corresponded to the theoretical values as follows:

Elementary analysis values:

| | C | H | N |
|---|---|---|---|
| Found: | 65.68% | 3.96% | 9.53% |
| Calculated: | 65.56% | 4.00% | 9.27% |

EXAMPLE 27

8.40 Grams (0.03 mol) of ethyl m-phenylene-bis-iminoacetate, 8.20 g (0.06 mol) of m-aminobenzoic acid, and 12.8 g (0.06 mol) of diphenyl carbonate were added to 50 ml of N-methylpyrrolidone, and the system was gradually heated in nitrogen gaseous current under stirring. The bath temperature reached 200°C. after approximately 2 hours, and at said temperature the system was reacted for 8 hours.

Then the phenol formed and the N-methylpyrrolidone which served as the solvent were distilled off in nitrogen current until a crystalline product started to be precipitated, while maintaining the bath temperature at 200°C. Upon cooling the system off to room temperature, the system was solidified. The crystalline product was recovered by filtration, washed with methanol and dried to provide 12.6 g (82% yield) of the object product. The crystal was not melted up to 300°C., and the infrared spectrum thereof showed the absorption of carboxyl group at 2300 – 3500 $cm^{-1}$, that from hydantoin bond at 1770 $cm^{-1}$, 1760 $cm^{-1}$, and 1715 $cm^{-1}$. Furthermore the characteristic absorption caused by the C=O stretching vibration of carboxyl group overlapped with that of the hydantoin at 1715 $cm^{-1}$, and was recognizable as the shoulder in the vicinity of 1700 $cm^{-1}$. The elementary analysis values of the product well corresponded to the theoretical values as follows:

Elementary analysis values:

| | C | H | N |
|---|---|---|---|
| Found: | 60.79% | 3.62% | 10.92% |
| Calculated: | 60.70% | 3.53% | 10.89% |

EXAMPLE 28

6.7 g (0.03 mol) of m-ethoxycarbonylaminobenzoic acid, 4.1 g (0.03 mol) of m-aminobenzoic acid, and 6.4 g (0.03 mol) of diphenyl carbonate were added to 50 ml of N-methylpyrrolidone, and the system was gradually heated in nitrogen current under stirring. The bath temperature reached 180°C. after approximately 2 hours, and the system was reacted for 12 hours at said temperature. Then the formed phenol and the N-methylpyrrolidone which served as the solvent were distilled off from the reaction mixture at 200°C., until a crystalline precipitate began to form. The system was solidified as allowed to cool off and stand, and whereupon the crystal was recovered by filtration, washed with methanol and dried, to provide 7.8 g (77% yield) of the object product which was not melted up to 300°C. The product's infrared spectrum showed the absorption by carboxylic acid at 2600 – 3500 $cm^{-1}$, that of hydantoin at 1765 $cm^{-1}$, 1730 $cm^{-1}$, and 1715 $cm^{-1}$, and also the absorption characteristic to C=O stretching vibration of carboxyl group at 1675 $cm^{-1}$. The elementary analysis values well corresponded to the theoretical values as follows:

Elementary analysis values:

| | C | H | N |
|---|---|---|---|
| Found: | 60.28% | 3.72% | 8.35% |
| Calculated: | 60.00% | 3.55% | 8.23% |

EXAMPLE 29

16.0 Grams (0.06 mol) of ethyl 3,5-dicarboxyphenyliminoacetate, 8.2 g (0.03 mol) of 3,9-bis(3-aminopropyl)-2,4,8,10-tetraoxaspiro(5,5) undecane, and 12.8 g (0.06 mol) of diphenyl carbonate were dissolved in 70 ml of cresol, and the solution was slowly heated to 150°C., consuming 3 hours. The system was allowed to react at 150°C. for 2 hours, 2 hours at 180°C., and 5 hours at 200°C. After the reaction the formed methanol and cresol were distilled off, and the residue was concentrated to be solidified. The solid was washed with methanol. The yield was 17.8 g (80%). The elementary analysis values well corresponded to the theoretical values as follows:

Elementary analysis values:

|  | C | H | N |
|---|---|---|---|
| Found: | 53.21% | 4.96% | 7.32% |
| Calculated: | 53.22% | 4.87% | 7.52% |

EXAMPLE 30

7.40 Grams (0.02 mol) of ethyl diphenylmethane-4,4'-diiminoacetate, 5.48 g (0.04 mol) of m-aminobenzoic acid, and 25.7 g (0.12 mol) of di-m-cresyl carbonate were added to 50 ml of m-cresol, and the system was gradually heated in nitrogen current to 200°C., consuming an hour. After heating the system at 200°C. for 5 hours, 1 g of dibutyltin dilaurate was added, and the system was further heated for 10 hours at 240°C. Upon distilling the solvent off after the reaction, a solid product was precipitated, which was washed first with alcohol and then with acetone, to provide 12.3 g (92% yield) of the object product (m.p.: 125°C.). The infrared spectrum of the product showed the characteristic absorption of hydantoin at 1770 cm$^{-1}$ and 1720 cm$^{-1}$, and the C=O stretching vibration of nitrile ester overlapping with the hydantoin absorption at 1720 cm$^{-1}$. Whereas, the infrared spectrum of free bis-carboxylic acid corresponding to the product of this Example showed the characteristic absorption of carboxylic acid at 2300 cm$^{-1}$ - 3500 cm$^{-1}$ and 1675 cm$^{-1}$, which are absent in the spectrum of the present product. thus it was confirmed that the present product was esterified. The elementary analysis values well corresponded to the theoretical values as follows:

Elementary analysis values:

|  | C | H | N |
|---|---|---|---|
| Found: | 83.50% | 5.45% | 8.02% |
| Calculated: | 83.90% | 5.39% | 8.33% |

EXAMPLES 31 – 51

Polycarboxylic acids containing various hydantoin rings and aryl esters of such polycarboxylic acids were prepared in the manner similar to Examples 24 – 30. The types and quantities of the starting glycine derivatives (I), primary amines (II), and diaryl carbonates (III), as well as the structures of the products (IV) were as given below. The reaction conditions, yields, and the melting points, elementary analysis values, and characteristic absorptions in infrared spectra of the products were as shown in Table 2.

Example 31

| (I) |  | 4.46 g (0.02 mol) |
| (II) | NH$_2$–(CH$_2$)$_6$–NH$_2$ | 1.16 g (0.01 mol) |
| (III) |  | 4.28 g (0.02 mol) |
| (IV) | 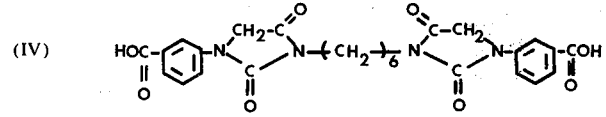 | |

Example 32

| (I) |  | 4.46 g (0.02 mol) |
| (II) |  (cis/trans = 30/70) | 2.10 g (0.01 mol) |
| (III) |  | 4.28 g (0.02 mol) |

Example 32-continued
(IV) 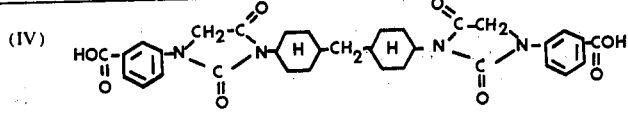
Example 33
(I) 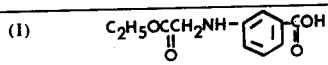  2.23 g (0.01 mol)
(II) 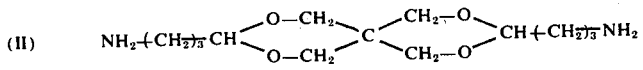  1.37 g (0.005 mol)
(III)   2.14 g (0.01 mol)
(IV) 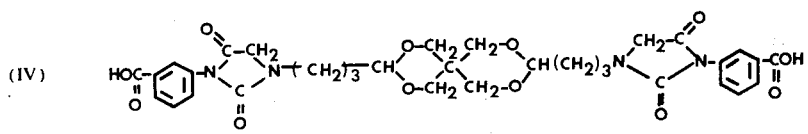
Example 34
(I) 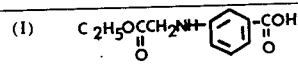  4.46 g (0.02 mol)
(II)   2.00 g (0.01 mol)
(III) 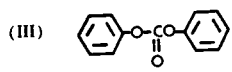  4.28 g (0.02 mol)
(IV) 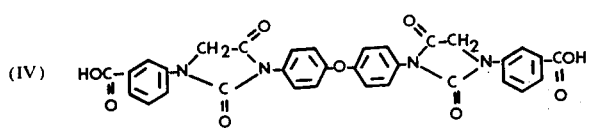
Example 35
(I) 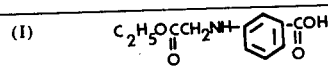  4.46 g (0.02 mol)
(II) 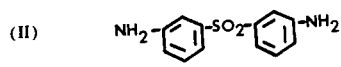  2.48 g (0.01 mol)
(III) 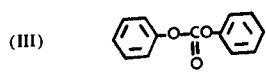  4.28 g (0.02 mol)
(IV) 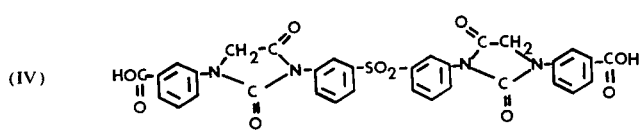

Example 36

| | | |
|---|---|---|
| (I) | $C_2H_5OCCH_2NH-\text{C}_6H_4-COH$ (with C=O groups) | 2.23 g (0.01 mol) |
| (II) | $NH_2$-Ph-C(=N)(NH)-benzimidazole-benzimidazole-C(=N)(NH)-Ph-$NH_2$ | 2.08 g (0.005 mol) |
| (III) | Ph-O-C(=O)-O-Ph (diphenyl carbonate) | 2.14 g (0.01 mol) |
| (IV) | HOOC-Ph-N(CH$_2$C=O)(C=O)-N-Ph-[benzimidazole-benzimidazole]-Ph-N(C=O)(C=OCH$_2$)-N-Ph-COOH | |

Example 37

| | | |
|---|---|---|
| (I) | $C_2H_5OCCH_2NH-\text{C}_6H_4-COH$ | 4.46 g (0.02 mol) |
| (II) | $NH_2$-Ph-NHC(=O)-Ph-$NH_2$ | 2.27 g (0.01 mol) |
| (III) | Ph-O-C(=O)-O-Ph | 4.28 g (0.02 mol) |
| (IV) | HOOC-Ph-N(CH$_2$C=O)(C=O)-N-Ph-NHC(=O)-Ph-N-(C=O)(C=OCH$_2$)-N-Ph-COOH | |

Example 38

| | | |
|---|---|---|
| (I) | $C_2H_5OCCH_2NH-\text{C}_6H_4-COH$ | 4.46 g (0.02 mol) |
| (II) | $NH_2$-benzothiazole-$NH_2$ | 1.65 g (0.01 mol) |
| (III) | Ph-O-C(=O)-O-Ph | 4.28 g (0.02 mol) |

Example 38-continued
(IV) 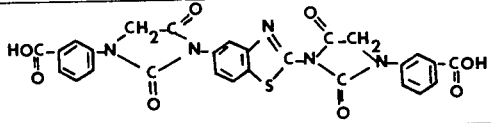
Example 39
(I) 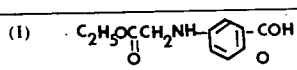  4.46 g (0.02 mol)
(II) 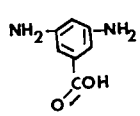  1.52 g (0.01 mol)
(III) 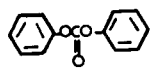  4.28 g (0.02 mol)
(IV) 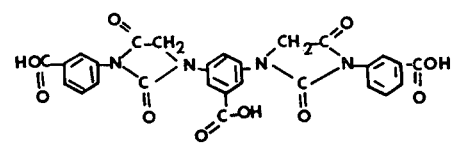
Example 40
(I) 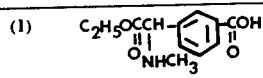  4.74 g (0.02 mol)
(II) 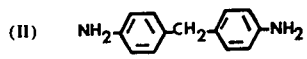  1.98 g (0.01 mol)
(III) 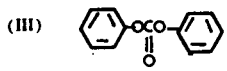  4.28 g (0.02 mol)
(IV) 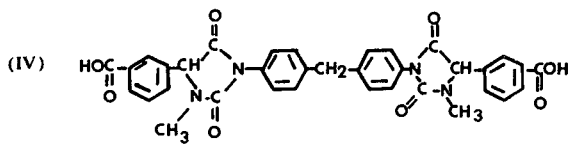
Example 41
(I) 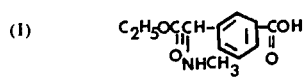  4.74 g (0.02 mol)
(II) 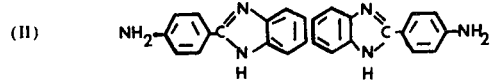  4.16 g (0.01 mol)

Example 41-continued
(III)  4.28 g (0.02 mol)
(IV) 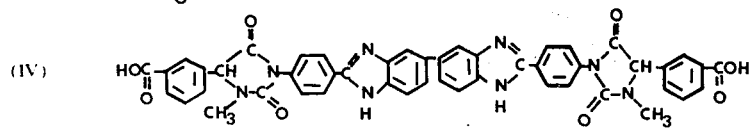
Example 42
(I)  4.74 g (0.02 mol)
(II) 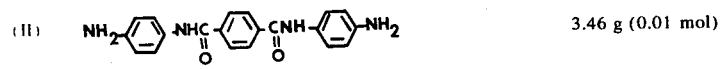 3.46 g (0.01 mol)
(III)  4.28 g (0.02 mol)
(IV) 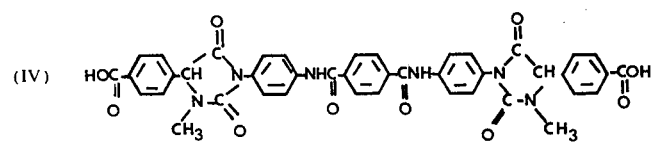
Example 43
(I) 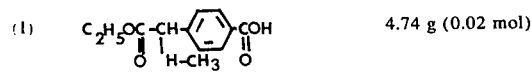 4.74 g (0.02 mol)
(II) 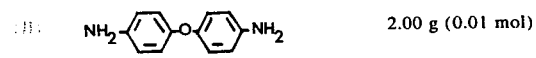 2.00 g (0.01 mol)
(III)  4.28 g (0.02 mol)
(IV) 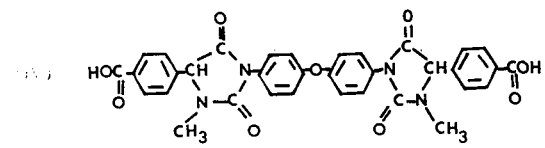
Example 44
(I) 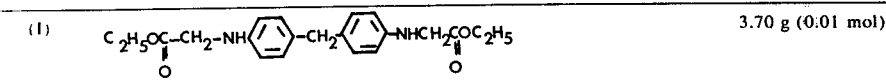 3.70 g (0.01 mol)
(II)  2.62 g (0.02 mol)

Example 44-continued
| | | |
|---|---|---|
| (III) | 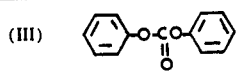 | 4.28 g (0.02 mol) |
| (IV) | 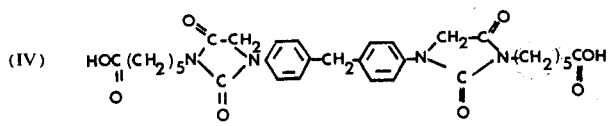 | |
Example 45
| | | |
|---|---|---|
| (I) | 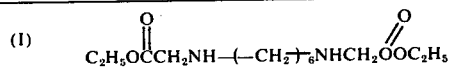 | 5.37 g (0.0186 mol) |
| (II) | 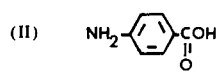 | 5.11 g (0.0372 mol) |
| (III) | 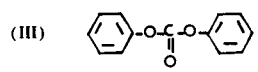 | 7.96 g (0.0972 mol) |
| (IV) | 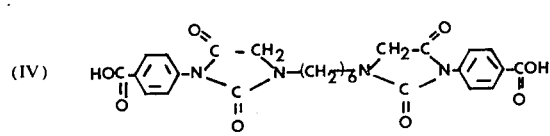 | |
Example 46
| | | |
|---|---|---|
| (I) | 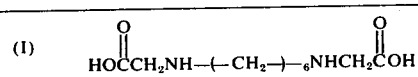 | 4.64 g (0.02 mol) |
| (II) | 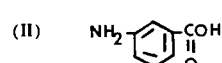 | 5.48 g (0.04 mol) |
| (III) | 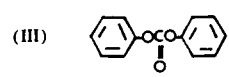 | 4.28 g (0.04 mol) |
| (IV) | 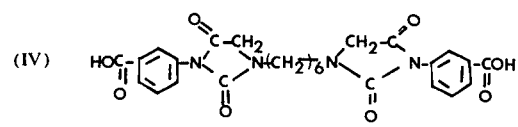 | |
Example 47
| | | |
|---|---|---|
| (I) | 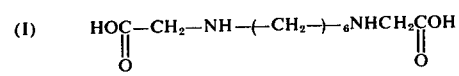 | 4.64 g (0.02 mol) |
| (II) | 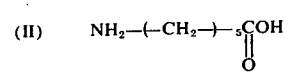 | 5.24 g (0.04 mol) |
| (III) | 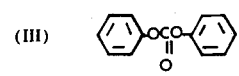 | 8.56 g (0.04 mol) |
| (IV) | 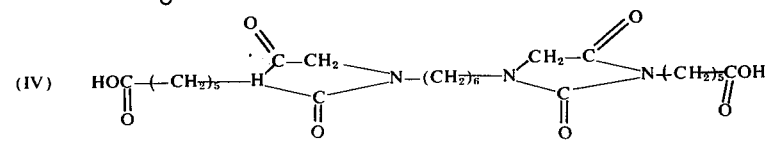 | |

Example 48
| | | |
|---|---|---|
| (I) |  | 0.378 g (0.0015 mol) |
| (II) |  | 0.411 g (0.003 mol) |
| (III) |  | 0.642 g (0.003 mol) |
| (IV) | 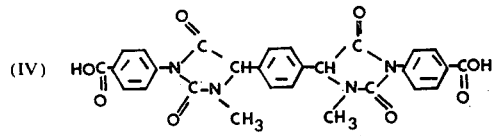 | |
Example 49
| | | |
|---|---|---|
| (I) | 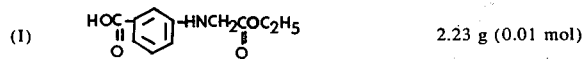 | 2.23 g (0.01 mol) |
| (II) |  | 1.31 g (0.01 mol) |
| (III) |  | 2.14 g (0.01 mol) |
| (IV) | 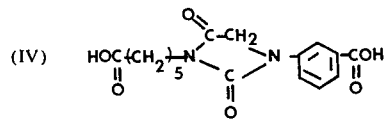 | |
Example 50
| | | |
|---|---|---|
| (I) | 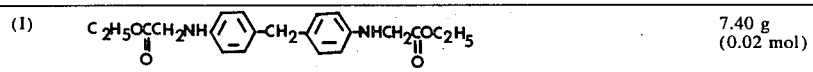 | 7.40 g (0.02 mol) |
| (II) |  | 5.48 g (0.04 mol) |
| (III) |  | 17.12 g (0.08 mol) |
| (IV) | 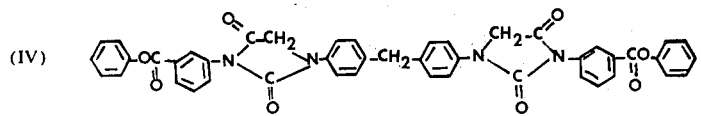 | |
Example 51
| | | |
|---|---|---|
| (I) | 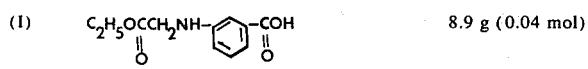 | 8.9 g (0.04 mol) |
| (II) | 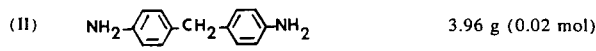 | 3.96 g (0.02 mol) |
| (III) |  | 17.1 g (0.08 mol) |

Example 51-continued (IV) 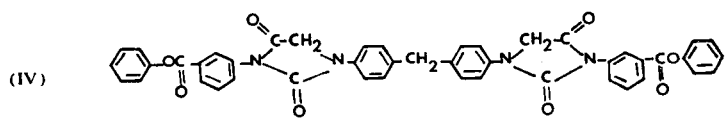

Table 2

| Ex. No. | Solvent (ml) | Reaction Temp./Reaction Time (°C./hr.) | Yield (%) | Melting Point (°C.) | Wavelengths of Characteristic Absorptions (cm$^{-1}$) | | C | H | N | S |
|---|---|---|---|---|---|---|---|---|---|---|
| 31 | Cresol (15) | 200/8 | 90 | 295 | 2300 – 3500, 1680 (COOH) 1770, 1715 (hydantoin) | Calcd. Found | 59.53 59.32 | 5.38 5.28 | 10.68 10.36 | — — |
| 32 | Cresol (15) | 200/8 | 80 | 181 – 245 | 2300 – 3600, 1700 (COOH) 1770, 1710 (hydantoin) | Calcd. Found | 64.27 64.53 | 5.88 5.76 | 9.09 9.23 | — — |
| 33 | Cresol (5) | 200/5 | 82 | 165 – 6 | 1770, 1720 (hydantoin) 2500 – 3600, 1710 (COOH) | Calcd. Found | 58.23 58.63 | 5.33 5.42 | 8.23 8.01 | — — |
| 34 | Cresol (20) | 200/3 | 25 | 300< | 2200 – 3700, 1680 (COOH) 1770, 1720 (hydantoin) | Calcd. Found | 70.84 70.92 | 4.09 4.23 | 10.33 10.58 | — — |
| 35 | Cresol (10) | 200/4 | 35 | 286 – 7 | 2300 – 3700, 1680 (COOH) 1780, 1725 (hydantoin) | Calcd. Found | 58.71 58.92 | 3.39 3.16 | 8.56 8.48 | 4.90 5.30 |
| 36 | Cresol (13) | 200/4 | 54 | 300< | 200 – 3700 (COOH, imidazole) 1770, 1710 (hydantoin) | Calcd. Found | 67.31 67.55 | 3.41 3.21 | 13.65 13.88 | — — |
| 37 | Cresol (10) | 200/4 | 71 | 300< | 2000 – 3700, 1690 (COOH) 1775, 1720 (hydantoin) | Calcd. Found | 62.56 62.83 | 3.66 3.83 | 11.06 11.07 | — — |
| 38 | Cresol (10) | 200/6 | 44 | 270 | 3400, 1650 (amide) 2000 – 3500, 1670 (COOH) 1770, 1750, 1720 (hydantoin) 1590 (thiazole) | Calcd. Found | 56.74 56.83 | 3.00 3.35 | 12.26 12.31 | 5.61 6.03 |
| 39 | Cresol (20) | 200/5 | 66 | 300< | 2200 – 3700, 1690 (COOH) 1775, 1730 | Calcd. Found | 58.07 58.32 | 3.25 3.53 | 10.03 10.32 | — — |
| 40 | Cresol (20) | 200/5 | 72 | 300< | 2500 – 3500, 1680 (COOH) 1770, 1715 (hydantoin) | Calcd. Found | 66.45 66.46 | 4.46 4.95 | 8.86 8.93 | — — |
| 41 | Cresol (20) | 200/5 | 83 | 300< | 2500 – 3500, 1695 (COOH) 1770, 1715 (hydantoin) | Calcd. Found | 67.92 67.63 | 3.80 3.75 | 13.20 13.25 | — — |
| 42 | Cresol (20) | 200/5 | 63 | 300< | 2500 – 3500, 1695 (COOH) 1770, 1715 (hydantoin) 1660 (amide) | Calcd. Found | 64.61 64.73 | 4.13 4.23 | 10.77 10.78 | — — |
| 43 | Cresol (20) | 200/5 | 81 | 300< | 2500 – 3500, 1690 (COOH) 1700, 1715 (hydantoin) | Calcd. Found | 63.36 63.43 | 3.66 3.73 | 9.24 9.53 | — — |
| 44 | Cresol (10) | 200/6 | 68 | 210 – 211 | 2300 – 3600, 1700 (COOH) 1770, 1700 (hydantoin) | Calcd. Found | 62.82 62.75 | 6.12 6.08 | 9.45 9.32 | — — |
| 45 | Cresol (20) | 230/20 | — | Amorphous | 2000 – 3400, 1670 (COOH) 1770, 1720 (hydantoin) | Calcd. Found | 59.76 59.68 | 5.02 5.34 | 10.72 10.38 | — — |
| 46 | Cresol (30) | 230/30 | — | Crude | 2100 – 3600, 1690 (COOH) 1770, 1710 (hydantoin) | Calcd. Found | 59.76 59.68 | 5.02 5.32 | 10.72 10.93 | — — |
| 47 | Cresol (30) | 230/30 | — | Crude | 2500 – 3500, 1675 (COOH) 1770, 1710 (hydantoin) | Calcd. Found | 56.45 56.63 | 7.50 7.62 | 10.97 10.83 | — — |
| 48 | Cresol (5) | 220/13 | 38 | 300< | 2300 – 3500, 1680 (COOH) 1770, 1720 (hydantoin) | Calcd. Found | 61.99 61.53 | 4.09 4.86 | 10.33 10.66 | — — |
| 49 | Cresol (10) | 200/5 | 78 | 208 – 9 | 2300 – 3500, 1670 (COOH) 1760, 1710 (hydantoin) | Calcd. Found | 57.48 57.32 | 5.43 5.16 | 8.38 8.15 | — — |
| 50 | Cresol | 200/3 (after addition of 20 mg of LiOH) | 99 | 125 – 6 | 1775, 1725 (hydantoin) | Calcd. Found | 71.42 71.72 | 4.26 4.53 | 7.40 7.31 | — — |
| 51 | Cresol | do. | 100 | 141 – 2 | 1775, 1725 (hydantoin) | Calcd. | 71.42 | 4.26 | 7.40 | — |

Table 2-continued

| Ex. No. | Solvent (ml) | Reaction Temp./Reaction Time (°C./hr.) | Yield (%) | Melting Point (°C.) | Wavelengths of Characteristic Absorptions (cm$^{-1}$) | Elementary Analysis Values (%) | | | |
|---|---|---|---|---|---|---|---|---|---|
| | | | | | | | C | H | N | S |
| | (20) | | | | | Found | 71.72 | 4.53 | 7.14 | |

EXAMPLE 52

5.26 Grams (0.02 mol) of m-ethoxy carbonyl-methylaminobenzoic acid allyl ester, 1.98 g (0.01 mol) of 4,4'-diaminodiphenylmethane, and 4.28 g (0.02 mol) of diphenyl carbonate were added to 10 ml of cresol, and the system was slowly heated in nitrogen current under stirring to 200°C. The system was then reacted at 200°C. for 5 hours, while distilling off the by-produced ethanol. After the reaction the solvent and byproduced phenol were distilled off, and the residual solid was washed with a minor amount of methanol. Thus 4.2 g (62% yield) of a hydantoin ring-containing dicarboxylic acid diallyl ester was obtained, which had a melting point of 143°C. The infrared spectrum of the product showed the characteristic absorptions based on the carbonyl stretching vibration of hydantoin at 1770 cm$^{-1}$ and 1715 cm$^{-1}$, and that based on the allyl radical at 1640 cm$^{-1}$. Also the carbonyl stretching vibration of allyl ester was observed at 1715 cm$^{-1}$, was superposed with the hydantoin absorption. The elementary analysis values measured well corresponded with the theoretical values as follows:

Elementary analysis values:

| | C | H | N |
|---|---|---|---|
| Found: | 68.51% | 4.83% | 8.02% |
| Calculated: | 68.41% | 4.71% | 8.18% |

EXAMPLES 53 – 56

Polycarboxylic acid allyl esters containing various hydantoin rings were prepared in the manner similar to Example 52. The types and quantities of the starting glycine derivatives (I), primary amines (II), and diaryl carbonates (III), as well as the structures of the products were enumerated below. Also the reaction conditions, yields, and the melting points, elementary analysis values, and characteristic absorptions in infrared spectra of the products, were shown in Table 3.

Example 53

(I) CH$_2$=CHCH$_2$OC-⟨⟩-NHCH$_2$COC$_2$H$_5$     5.26 g (0.02 mol)

(II) NH$_2$-⟨⟩-CH$_2$-⟨⟩-NH$_2$     1.98 g (0.01 mol)

(III) ⟨⟩-OCO-⟨⟩     4.28 g (0.02 mol)

(IV) CH$_2$=CHCH$_2$OC-⟨⟩-N(CH$_2$-CO)(CO)N-⟨⟩-CH$_2$-⟨⟩-N(CO)(CO-CH$_2$)N-⟨⟩-COCH$_2$CH=CH$_2$

Example 54

(I) C$_2$H$_5$OC-CH$_2$NH-⟨⟩-CH$_2$-⟨⟩-NHCH$_2$COC$_2$H$_5$     3.70 g (0.01 mol)

(II) CH$_2$=CHCH$_2$OC-⟨⟩-NH$_2$     3.54 g (0.02 mol)

(III) ⟨⟩-O-C(=O)-O-⟨⟩     4.28 g (0.02 mol)

(IV) CH$_2$=CHCH$_2$OC-⟨⟩-N(C-CH$_2$)(CO)N-⟨⟩-CH$_2$-⟨⟩-N(CH$_2$-C)(CO)N-⟨⟩-COCH$_2$CH=CH$_2$

Example 55

| | | |
|---|---|---|
| (I) | 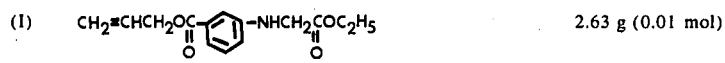 | 2.63 g (0.01 mol) |
| (II) |  | 1.77 g (0.01 mol) |
| (III) |  | 2.14 g (0.01 mol) |
| (IV) | 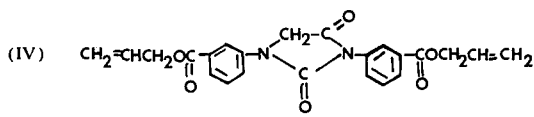 | |

Example 56

| | | |
|---|---|---|
| (I) | 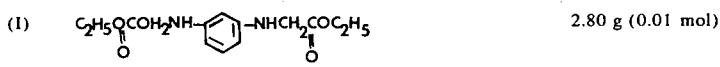 | 2.80 g (0.01 mol) |
| (II) |  | 3.54 g (0.02 mol) |
| (III) |  | 4.28 g (0.02 mol) |
| (IV) | 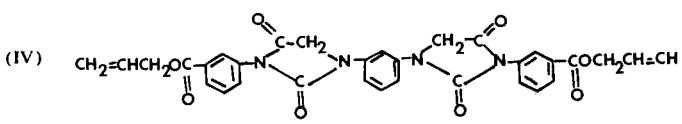 | |

Table 3

| Ex. | Solvent (ml) | Reaction Temp. /Reaction Time (°C./hr.) | Yield (%) | Melting Point (°C.) | Wavelengths of Characteristic Absorptions (cm$^{-1}$) | | Elementary Analysis Values (%) | | |
|---|---|---|---|---|---|---|---|---|---|
| | | | | | | | C | H | N |
| 53 | Cresol (10) | 200/5 | 73 | 300< | 1765, 1715 (hydantoin) 1715 (ester) 1640 (allyl) | Calcd. Found | 68.41 68.52 | 4.71 4.68 | 8.18 8.08 |
| 54 | Cresol (20) | 200/5 | 76 | 167 | 1765, 1715 (hydantoin) 1715 (ester) 1640 (allyl) | Calcd. Found | 68.41 68.29 | 4.71 4.91 | 8.18 8.32 |
| 55 | Cresol (10) | 200/5 | 45 | 112 | 1765, 1720 (hydantoin) 1720 (ester) 1640 (allyl) | Calcd. Found | 65.78 65.82 | 4.80 4.91 | 6.66 6.58 |
| 56 | Cresol (10) | 200/5 | 62 | 197 | 1765, 1720 (hydantoin) 1720 (ester) 1640 (allyl) | Calcd. Found | 64.64 64.53 | 4.41 4.23 | 9.42 9.36 |

EXAMPLE 57

5.02 Grams (0.02 mol) of ethyl p-ethoxycarbonyl-methylaminobenzoate, 1.98 g (0.01 mol) of 4,4'-diaminodiphenylmethane, and 4.28 g (0.02 mol) of diphenyl carbonate were added to 20 ml of cresol, and the system was slowly heated in nitrogen current under stirring. After the bath temperature reached 200°C., the system was reacted for subsequent 5 hours at said temperature, while distilling off the by-produced ethanol. After completion of the reaction the solvent and by-produced phenol were distilled off. When the distillation fairly advanced, methanol was added and the system was continuously stirred at room temperature, to allow precipitation of white solid. The precipitate was recovered by filtration and washed to provide 5.0 g (75% yield) of a hydantoin ring-containing dicarboxylic acid ethyl ester which was melting at 252° – 6°C. The infrared spectrum of the product showed the characteristic absorptions based on the carbonyl stretching vibration of hydantoin ring at 1780 cm$^{-1}$ and 1720 cm$^{-1}$. The elementary analysis values measured well corresponded to the theoretical values as follows:

Elementary analysis values:

|  | C | H | N |
|---|---|---|---|
| Found: | 67.52% | 4.96% | 8.23% |
| Calculated: | 67.26% | 4.88% | 8.48% |

EXAMPLES 58 – 61

Various hydantoin ring-containing polycarboxylic acid esters were prepared in the manner similar to Example 57. The types and quantities of the starting glycine derivatives (I), primary amines (II), and diaryl carbonate (III), as well as the structure of the product (VI) of the Examples were as enumerated below. Also the reaction conditions, yields, and the melting points, elementary analysis values, and characteristic absorptions in the infrared spectra of the products, are given in Table 4.

Example 58

| | | |
|---|---|---|
| (I) | 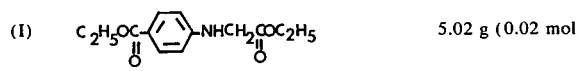 | 5.02 g (0.02 mol) |
| (II) | 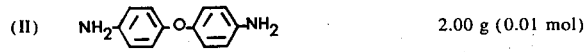 | 2.00 g (0.01 mol) |
| (III) |  | 4.28 g (0.02 mol) |
| (IV) | 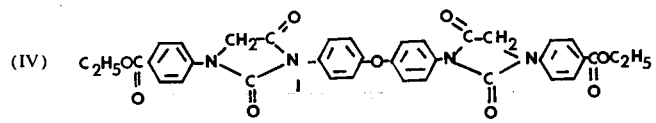 | |

Example 59

| | | |
|---|---|---|
| (I) | 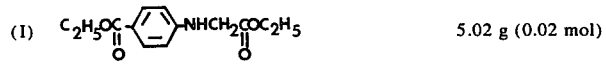 | 5.02 g (0.02 mol) |
| (II) | NH$_2$—(CH$_2$)—$_6$NH$_2$ | 1.16 g (0.01 mol) |
| (III) |  | 4.28 g (0.02 mol) |
| (IV) |  | |

Example 60

| | | |
|---|---|---|
| (I) | 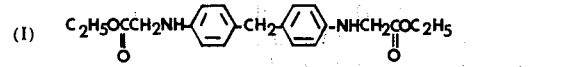 | 3.70 g (0.01 mol) |
| (II) | NH$_2$—(CH$_2$)—$_5$COC$_2$H$_5$ | 3.18 g (0.02 mol) |
| (III) |  | 4.28 g (0.02 mol) |

Example 60-continued

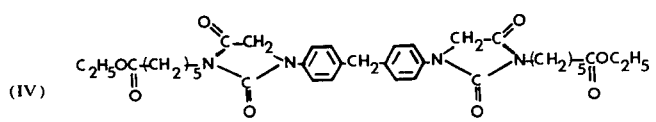

Example 61

(I) [structure with formula]     3.36 g (0.01 mol)

(II) $NH_2$-⟨⟩-$COC_2H_5$ (with =O)     3.30 g (0.02 mol)

(III) [diphenyl carbonate structure]     4.28 g (0.02 mol)

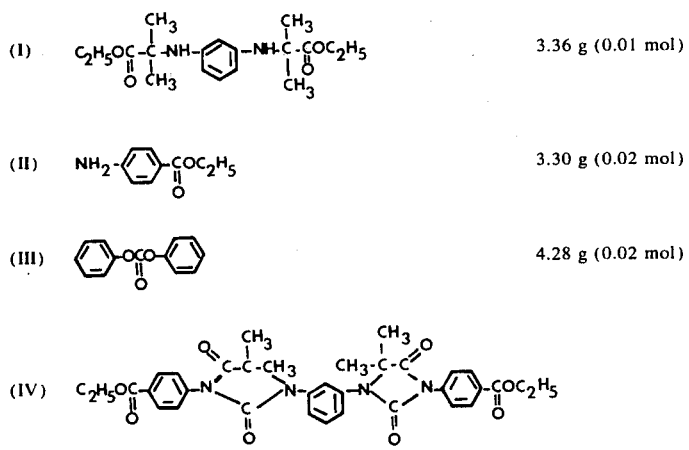

Table 4

| Ex. No. | Solvent (ml) | Reaction Temp./Reaction Time (°C./hr.) | Yield (%) | Melting Point (°C.) | Wavelengths of Characteristic Absorptions (cm$^{-1}$) | Elementary Analysis Values (%) | | | |
|---|---|---|---|---|---|---|---|---|---|
| | | | | | | | C | H | N |
| 58 | Cresol (20) | 170/10 | 63 | 267 – 269 | 1780, 1720 (hydantoin) | Calcd. | 65.25 | 4.56 | 8.46 |
| | | | | | | Found | 65.43 | 4.43 | 8.52 |
| 59 | Cresol (20) | 200/10 | 76 | 236 – 239 | 1780, 1725 (hydantoin) | Calcd. | 62.27 | 5.92 | 9.68 |
| | | | | | | Found | 62.31 | 6.01 | 9.72 |
| 60 | Cresol (20) | 200/10 | 63 | 116 | 1775, 1715 (hydantoin) | Calcd. | 64.80 | 6.84 | 8.64 |
| | | | | | | Found | 64.92 | 6.96 | 8.42 |
| 61 | Cresol (15) | 200/10 | 46 | 140 | 1775, 1715 (hydantoin) | Calcd. | 65.16 | 5.47 | 8.94 |
| | | | | | | Found | 65.28 | 5.51 | 8.73 |

EXAMPLE 62

9.0 Grams (0.04 mol) of m-ethoxycarbonylmethylaminobenzoic acid, 4.36 g (0.04 mol) of m-aminophenol, and 8.56 g (0.04 mol) of diphenyl carbonate were added to 25 ml of cresol, and the system was gradually heated in nitrogen atmosphere under stirring. Then the system was allowed to react at 200°C. for 4 hours. The by-produced ethanol was distilled off from the system as formed. After the reaction the solvent and by-produced phenol were distilled off. When the greatest part of the solvent and phenol was distilled off, methanol was added to the residue, and stirred continuously at room temperature. Thus a white precipitate was formed, which was recovered by filtration and washed with methanol to provide 7.8 g (62% yield) of hydantoin ring-containing hydroxycarboxylic acid. The hydroxycarboxylic acid had the melting point at 259° – 260°C., and its infrared spectrum showed the characteristic absorptions of carboxyl group at 2000 – 3500 cm$^{-1}$ and at 1700 cm$^{-1}$, that of hydroxyl group at 3400 cm$^{-1}$, and the characteristic absorptions based on hydantoin at 1760 cm$^{-1}$ and 1725 cm$^{-1}$. Thus the formation of hydantoin ring-containing hydroxycarboxylic acid was confirmed. The elementary analysis of the acid gave the results well corresponding to the theoretical values as follows:

Elementary analysis values:

| | C | H | N |
|---|---|---|---|
| Found: | 61.23% | 3.62% | 8.53% |
| Calculated: | 61.53% | 3.87% | 8.97% |

EXAMPLES 63 – 66

Various hydantoin ring-containing hydroxycarboxylic acids were formed in the manner similar to Example 62. The types and quantities of the starting glycine derivatives (I), primary amines (II), and diaryl carbonate (III) employed, as well as the structures of the products (IV) were as enumerated below. Also the reaction conditions, yields, and the melting points, elementary analysis values, and characteristic absorptions in the infrared spectra, of the products, are given in Table 5.

Example 63

| | | |
|---|---|---|
| (I) | HOC-C₆H₄-NHCH₂COC₂H₅ (with C=O groups) | 1.1 g (0.005 mol) |
| (II) | HO-C₆H₄-NH₂ | 0.55 g (0.005 mol) |
| (III) | C₆H₅-O-CO-O-C₆H₅ | 1.1 g (0.005 mol) |
| (IV) | HO-C₆H₄-N(hydantoin ring)N-C₆H₄-COOH | |

Example 64

| | | |
|---|---|---|
| (I) | HOC-C₆H₄-NHCH₂COC₂H₅ | 6.69 g (0.03 mol) |
| (II) | HO-C₆H₄-NH₂ | 3.27 g (0.03 mol) |
| (III) | C₆H₅-O-CO-O-C₆H₅ | 6.42 g (0.03 mol) |
| (IV) | HO-C₆H₄-N(hydantoin ring)N-C₆H₄-COOH | |

Example 65

| | | |
|---|---|---|
| (I) | HOC-C₆H₄-NHCH₂COC₂H₅ | 0.22 g (0.001 mol) |
| (II) | HO-C₆H₄-NH₂ | 0.11 g (0.001 mol) |
| (III) | C₆H₅-O-CO-O-C₆H₅ | 0.22 g (0.001 mol) |
| (IV) | HO-C₆H₄-N(hydantoin ring)N-C₆H₄-COOH | |

Example 66

(I) HOC-⟨⟩-NHCH₂COC₂H₅      4.46 g (0.02 mol)
     ‖                    ‖
     O                    O (II) HO―(CH₂)₂―O―(CH₂)₂―NH₂      2.10 g (0.02 mol)

(III) ⟨⟩-OCO-⟨⟩      4.28 g (0.02 mol)
          ‖
          O (IV) HO(CH₂)₂O(CH₂)₂-N⟨C-CH₂⟩N-⟨⟩-COH
                        ‖       ‖
                        O       O

Table 5

| Ex. No. | Solvent (ml) | Reaction/ Temp. / Reaction Time (°C./Hr.) | Yield (%) | Melting Point (°C.) | Wavelenghts of Characteristic Absorptions (cm⁻¹) | Elementary Analysis Values (%) | | | |
|---|---|---|---|---|---|---|---|---|---|
| | | | | | | | C | H | N |
| 63 | Cresol (3) | 200/5 | 71 | 300< | 2000-3500, 1700 (COOH) 3400 (OH) 1770, 1720 (hydantoin) | Calcd. Found | 61.53 61.62 | 3.87 3.76 | 8.97 8.63 |
| 64 | Cresol (20) | 200/4 | 81 | 300< | 2000-3600, 1675 (COOH) 3400 (OH) 1770, 1710 (hydantoin) | Cald. Found | 61.53 61.86 | 3.87 3.63 | 8.97 8.72 |
| 65 | Cresol (3) | 200/5 | 62 | 260 | 2300-3500, 1690 (COOH) 3400 (OH) 1770, 1720 (hydantoin) | Calcd. Found | 61.53 60.96 | 3.87 3.75 | 8.97 8.81 |
| 66 | Cresol (20) | 230/8 | 93 | Amorphous | 2300-3700, 1710 (COOH) 3350 (OH) 1770, 1710 (hydantoin) | Calcd. Found | 54.54 54.63 | 5.23 5.01 | 9.09 9.35 |

EXAMPLE 67

22.2 g (0.06 mol) of ethyl diphenylmethane-4,4'-diiminoacetate, 13.1 g (0.12 mol) of m-aminophenol, and 25.7 g (0.12 mol) of diphenyl carbonate were added to 25 ml of cresol, and the system was gradually heated to 200°C. under stirring. At said temperature the system was allowed to react for 5 hours, while distilling off the by-produced ethanol. After the reaction the solvent and by-produced phenol were distilled off, and the residue was treated with a large excess of ether to be crystallized. The crystalline precipitate was recovered by filtration and washed to provide 23.3 g (71%) of hydantoin ring-containing diol having the melting point at 235° - 237°C. The infrared spectrum of the product showed the characteristic absorption of hydroxyl group at 3400 cm⁻¹, and that of hydantoin at 1770 cm⁻¹ and 1715 cm⁻¹, confirming the formation of hydantoin ring-containing diol. The elementary analysis gave the results well corresponding to the theoretical values as follows:

Elementary analysis values:

|  | C | H | N |
|---|---|---|---|
| Found: | 67.88% | 4.43% | 10.07% |
| Calculated: | 67.87% | 4.41% | 10.21% |

EXAMPLES 68 – 70

Various hydantoin ring-containing diols were prepared in the manner similar to Example 67. The types and quantities of the starting glycine derivatives (I), primary amines (II), and diaryl carbonates (III) employed, as well as the structures of the products (IV) were as enumerated below. Also the reaction conditions, yields, and the melting points, elementary analysis values, and the characteristic absorptions in infrared spectra of the products, were as given in Table 6.

Example 68

(I) C₂H₅OCCH₂NH-⟨⟩-NHCH₂COC₂H₅      5.60 g (0.02 mol)
      ‖                    ‖
      O                    O (II) HO-⟨⟩-NH₂      4.36 g (0.04 mol)

(III) ⟨⟩-O-CO-⟨⟩      8.56 g (0.04 mol)
           ‖
           O

Example 68-continued (IV) 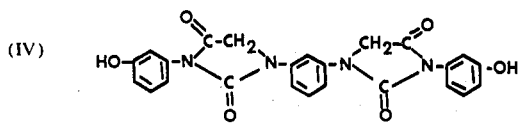

Example 69

(I) HO-⟨⟩-O-⟨⟩-NHCH₂CO₂H₅     0.574 g (0.002 mol)

(II) HO-⟨⟩-O-⟨⟩-NH₂     0.402 g (0.002 mol)

(III) ⟨⟩-O-CO-O-⟨⟩     0.428 g (0.002 mol)

(IV) 

Example 70

(I) C₂H₅OCCH₂NH-⟨⟩-CH₂-⟨⟩-NHCH₂COC₂H₅     7.40 g (0.02 mol)

(II) HO—(CH₂)—₂O—CH₂)—₂NH₂     4.20 g (0.04 mol)

(III) ⟨⟩-O-CO-O-⟨⟩     8.56 g (0.04 mol)

(IV) 

Table 6

| Ex. No. | Solvent (ml) | Reaction/ Temp. / Reaction / Time (°C./Hr.) | Yield (%) | Melting Point (°C.) | Wavelengths of Characteristic Absorptions (cm⁻¹) | Elementary Analysis Values (%) | | | |
|---|---|---|---|---|---|---|---|---|---|
| | | | | | | | C | H | N |
| 68 | Cresol (25) | 190/5 | 75 | 118–124 | 3400 (OH) 1765, 1710 (hydantoin) | Calcd. Found | 62.82 62.96 | 3.96 3.75 | 12.22 12.12 |
| 69 | Cresol (2.5) | 190/8 | 83 | 232–235 | 3400 (OH) 1775, 1705 (hydantoin) | Calcd. Found | 69.22 69.15 | 4.30 4.52 | 5.98 5.96 |
| 70 | Cresol (20) | 220/8 | 92 | 60 (sinter) 80 (flow) | 3350 (OH) 1760, 1705 (hydantoin) | Calcd. Found | 59.99 59.38 | 5.97 5.92 | 10.37 10.21 |

We claim:
1. A process for making monomeric hydantoin derivatives containing in their molecules at least one hydantoin ring (H) of the formula (H) below:

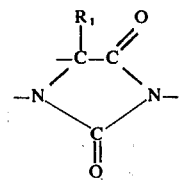

(H)

selected from the group consisting of

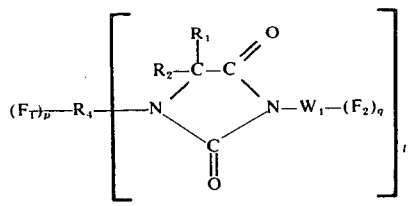
(IV-1),

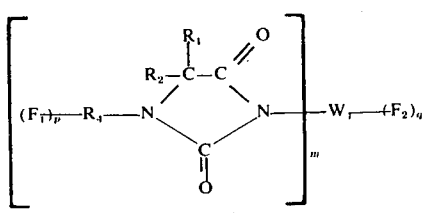
(IV-2),

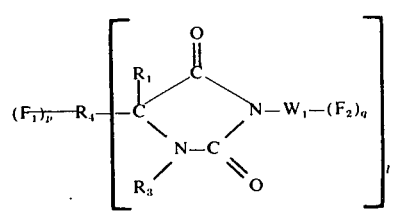
(IV-3), and

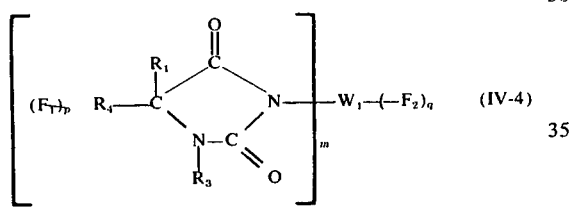
(IV-4)

wherein $R_1$, $R_2$ and $R_3$ may be the same or different and each denotes a hydrogen atom or a monovalent organic group selected from aliphatic groups of 1 to 20 carbon atoms, alicyclic groups of 3 to 20 carbon atoms and aromatic groups of 6 to 20 carbon atoms, said organic group optionally containing one or two hetero-elements selected from oxygen, nitrogen, and sulfur, $R_4$ denotes hydrogen atom or a $(l+p)$valent saturated or unsaturated aliphatic, alicyclic, aromatic, or heterocyclic group of 1 to 20 carbon atoms, which may contain 1 to 4 hetero-elements selected from oxygen, nitrogen, sulfur, phosphorus, or silicon atoms, the $(l+p)$ valency bonding with the carbon atoms, $W_1$ denotes hydrogen atom or a $(m+q)$ valent saturated or unsaturated aliphatic, alicyclic, aromatic, or heterocyclic group of 1 to 20 carbon atoms, which may contain 1 to 4 hetero-elements selected from oxygen, nitrogen, sulfur, phosphorus, or silicon atoms, the $(m+q)$ valency bonding with carbon atoms, $l$ is an integer of 1 to 5,
$p$ is an integer of 0 to 5,
$m$ is an integer of 1 to 5,
$q$ is an integer of 0 to 5,
$F_1$ and $F_2$ may be the same or different and each denotes halogen atom, nitro group (—$NO_2$), nitrile group (—CN), tertiary amino group,

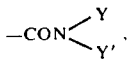

—OY, —SY, —COY, —OCOY, and —COOY wherein Y and Y' may be the same or different, and each denotes hydrogen atom or a monovalent organic radical selected from aliphatic, alicyclic, and aromatic hydrocarbon residues of 1 to 20 carbon atoms, which may contain 1 to 4 hetero atoms selected from oxygen, nitrogen, and sulfur, which comprises reacting
1. a glycine derivative (I) of the formula (I-1) or (I-2) below:

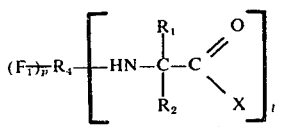
(I-1)

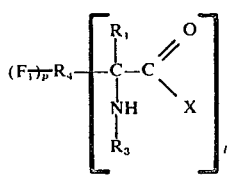
(I-2)

in which $F_1$, $p$, $R_1$, $R_2$, $R_3$, $R_4$, and $l$ have the previously given meanings, and X is selected from the group consisting of —OA, —SA, —NHA, and —N(A)$_2$ wherein A is a hydrogen atom or a monovalent hydrocarbon group selected from aliphatic, alicyclic and aromatic hydrocarbons of 1 to 7 carbon atoms, 2. an amine (II) of the formula (II-1)

$(F_2)_q\text{—}W_1\text{—}(NH_2)_m$ (II-1)

in which $W_1$, $F_2$, $q$, and $m$ have the previously given meanings, and 3. a diaryl carbonate (III) of the formula

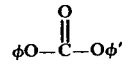
(III)

in which $\phi$ and $\phi'$ may be the same or different, and each stands for a monovalent aromatic radical with the proviso that
4. the above three reactants are selected such that at least one of $l$ and $m$ is 1; whereby when $l$ and $m$ are each 1 the compounds of formulae (IV-1) and (IV-2) and the compounds of formulae (IV-3) and (IV-4) respectively become identical and when $l$ is 2 to 5 and $m$ is 1 a compound of formula (IV-1) or (IV-3) is obtained and when $m$ is 2 to 5 and $l$ is 1 a compound of formula (IV-2) or (IV-4) is obtained.

2. The process for making monomeric hydantoin derivatives according to claim 1 wherein, the formulae (IV-1), (IV-2), (IV-3) and (IV-4),
$l$ and $m$ are each 1,
said monomeric hydantoin derivative having the formula

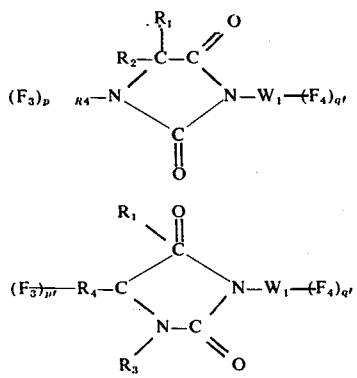

(IV-5)

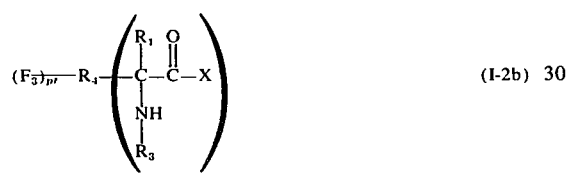

(IV-6)

which comprises reacting
1. a glycine derivative of the formula (I-1b) or (I-2b) below:

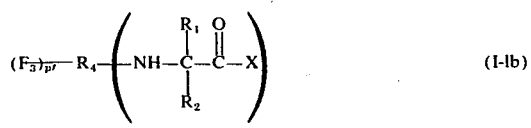

(I-1b)

or

(I-2b)

wherein $R_1$, $R_2$, $R_3$, $R_4$, and X have the previously given meanings, $(F_3)_{p'}$ is an hydroxyl group (—OH) or one or two —COOY radicals, provided that when $(F_3)_{p'}$ is two —COOY radicals, the two —COOY radicals are respectively linked with two adjacent carbon atoms in $R_4$, Y has the previously given meaning, and
$p'$ is 1 or 2, with
2. a primary amine of formula (II-3)

$(F_4)_{q'}$—$W_1$— $NH_2$      (II-3)

in which $(F_4)_{q'}$ is an hydroxy group (—OH) or one or two —COOY radicals, provided that when $(F_4)_{q'}$ is two —COOY radicals, the two —COOY radicals are respectively linked with two adjacent carbon atoms in $W_1$, $q'$ is a positive integer of 1 or 2, and
Y and $W_1$ have the previously given meanings, and
3. said diaryl carbonate of formula (III).

3. The process for making monomeric hydantoin derivatives according to claim 1 which are difunctional, said difunctional monomeric hydantoin derivatives selected from the group consisting of compounds of formula (IV-7) or (IV-8)

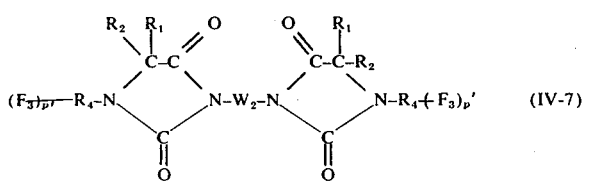

(IV-7)

or

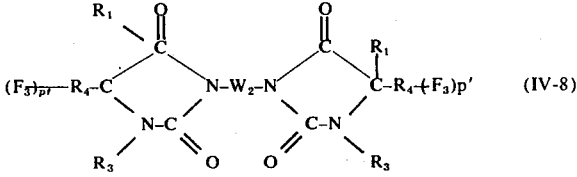

(IV-8)

in which $R_1$, $R_2$, $R_3$ and $R_4$ have the previously given meanings, $(F_3)_{p'}$ is an hydroxyl group (-OH) or one or two —COOY radicals, provided that when $(F_3)_{p'}$ stands for two —COOY radicals, the two —COOY radicals are respectively linked with two adjacent carbon atoms in $R_4$, $p'$ is a positive integer of 1 or 2, and
$W_2$ corresponds to the above-defined $W_1$ when $q=0$ and $m=2$, said process comprising reacting
1. a glycine derivative of the formula (I-1b) or (I-2b) below:

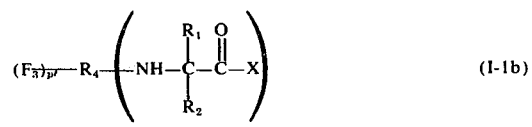

(I-1b)

or

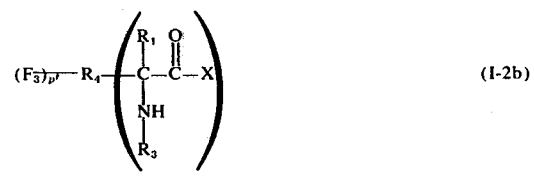

(I-2b)

wherein $R_1$, $R_2$, $R_3$, $R_4$, X and $(F_3)_{p'}$ have the previously given meanings, with
2. a primary diamine of formula (II-4)

$H_2N$ — $W_2$ — $NH_2$      (II-4)

wherein $W_2$ is as defined above and
3. said diaryl carbonate of formula (III) at a molar ratio of said glycine (1) to said primary diamine (2) of about 2 to 1.

4. The process for making monomeric hydantoin derivatives according to claim 1 which are difunctional, said difunctional monomeric hydantoin derivative selected from the group consisting of compounds of formula (IV-9) or (IV-10)

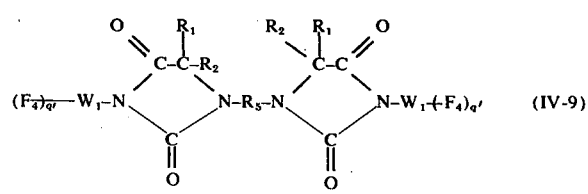

(IV-9)

or

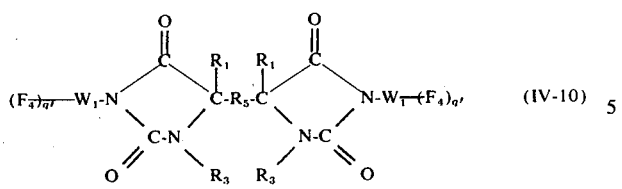

(IV-10)

in which $R_1$, $R_2$, $R_3$ and $W_1$ have the previously given meanings, $+F_4)_{q'}$ is an hydroxyl group (—OH) or one or two —COOY radicals, provided that when $(F_4)_{q'}$— stands for two —COOY radicals, the two —COOY radicals are respectively linked with two adjacent carbon atoms in $W_1$, $q'$ is 1 or 2, and $R_5$ corresponds to the above-defined $R_4$ when $p=0$ and $l=2$, said process comprising reacting 1. a bis-glycine derivative of formula (I-1c) or (I-2c)

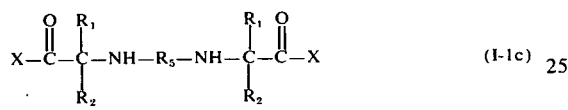

or

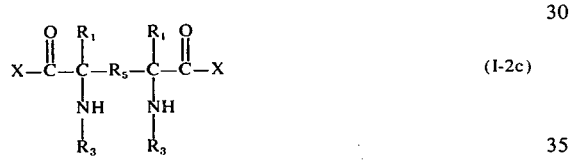

in which $R_1$, $R_2$, $R_5$ and X have the previously given meanings, with 2. a primary diamine compound of formula (II-3)

in which $(F_4)_{q'}$— and $W_1$ have the previously given meanings, and 3. said diaryl carbonate of formula (III) at a molar ratio of said primary amine compound (2) of formula (II-3) to said bisglycine derivative (1) of about 2:1.

5. The process for making monomeric hydantoin derivatives according to claim 1 wherein $R_1$, $R_2$ and $R_3$ may be the same or different and are selected from the group consisting of hydrogen, methyl, ethyl, propyl, butyl, cyclohexyl,

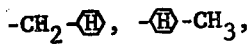

phenyl, benzyl, toluyl, naphthyl,

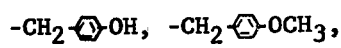

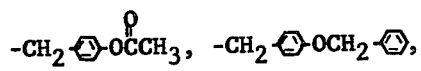

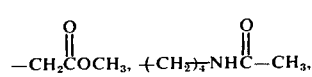

—$CH_2CH_2SCH_3$ and

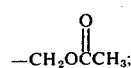

$R_4$ and $W_1$ may be the same or different and are hydrogen atom or the residue of a hydrocarbon selected from the group consisting of $CH_4$, $CH_3CH_3$, $CH_2=CH_2$, $CH_3.CH_2.CH_3$, $CH_2=CH—CH_3$, $CH_3CH_2CH_2CH_3$, $CH_2=CH-CH=CH_2$, $CH_3(CH_2)_4CH_3$, $CH_3(CH_2)_3CH_3$,

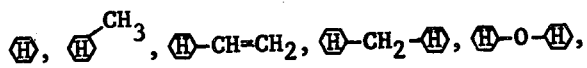

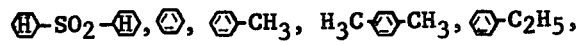

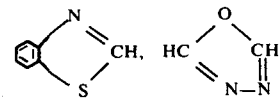

wherein M is selected from the group consisting of —O—, lower alkylene of 1–4 carbon atoms, —NH-CO—, —SO$_2$—, —CO—,

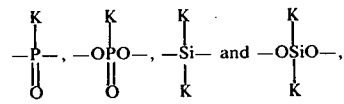

wherein K is a monovalent organic radical selected from the group consisting of $CH_3$- and

Y and Y' may be the same or different and each represents a hydrogen atom or a residue of a hydrocarbon selected from the group consisting of $CH_4$, $CH_3(CH_2)_3CH_3$, $CH_2=CH—CH_3$, and

and

A is selected from the group consisting of hydrogen, methyl, ethyl, phenyl and benzyl.

6. The process for making hydantoin derivatives according to claim 1, wherein the specified compounds (I), (II), and (III) are mutually reacted at such a quantitative ratio that the glycine residue (G) in the glycine derivative (I) is made substantially equimolar to the primary amino group in the amine (II), and also at least equimolar to the glycine residue (G) of diaryl carbonate (III).

7. The process for making hydantoin derivatives according to claim 1, wherein the glycine derivative (I), amine (II), and the diaryl carbonate (III) are reacted under heating, in the absence of a solvent or in the presence of an inert solvent.

8. The process of claim 1 wherein $(F_3)_{q'}$ and $(F_4)_{q''}$ are each —COOY'' wherein Y'' is hydrogen or an alkyl of 1 to 4 carbon atoms, further comprising employing an excess of said diaryl carbonate of formula (III), said diaryl carbonate being used in the formation of said hydantoin ring and the excess being used to form a diaryl ester of said hydantoin derivative of the formula

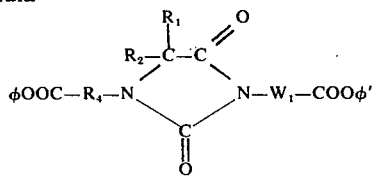

or

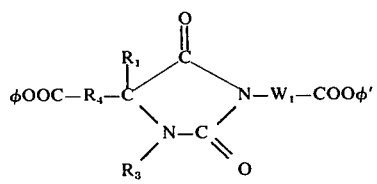

wherein $R_1$, $R_2$, $R_3$, $R_4$, $W_1$, $\phi$ and $\phi'$ have the previously given meanings.

9. The process of claim 3 wherein $(F_3)_{p'}$ is —COOY'' wherein Y'' is hydrogen or alkyl of 1 to 4 carbon atoms, further comprising employing an excess of said diaryl carbonate of formula (III), said diaryl carbonate being used in the formation of said hydantoin ring and the excess being used to form a diaryl ester of said hydantoin derivative of the formula

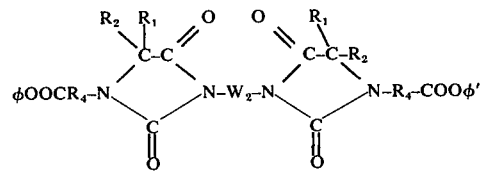

or

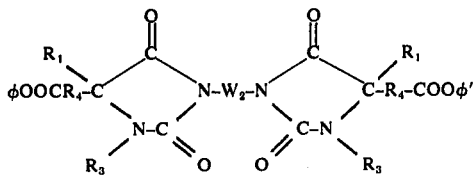

wherein $R_1$, $R_2$, $R_3$, $R_4$, $W_2$, $\phi$ and $\phi'$ have the previously given meanings.

10. The process of claim 4 wherein $(F_4)_{q'}$ is —COOY'' wherein Y'' is hydrogen or an alkyl of 1 to 4 carbon atoms, further comprising employing an excess of said diaryl carbonate of formula (III), said diaryl carbonate being used in the formation of said hydantoin ring and the excess being used to form a diaryl ester of said hydantoin derivative of the formula

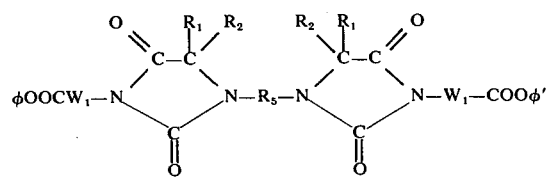

or

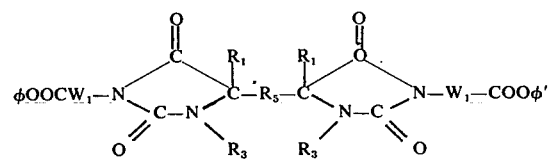

wherein $R_1$, $R_2$, $R_3$, $R_4$, $W_1$, $\phi$ and $\phi'$ have the previously given meanings.

11. The process for making hydantoin derivatives according to claim 1 wherein the glycine derivative (I), amine (II) and diaryl carbonate (II) are reacted under heating in the presence of an inert solvent.

* * * * *

UNITED STATES PATENT OFFICE
CERTIFICATE OF CORRECTION

Patent No. __3,946,033__  Dated __March 23, 1976__

Inventor(s) __IWATA, ET AL.__

It is certified that error appears in the above-identified patent and that said Letters Patent are hereby corrected as shown below:

Column 81, delete formula (IV-5) in its entirety and insert the following therefor:

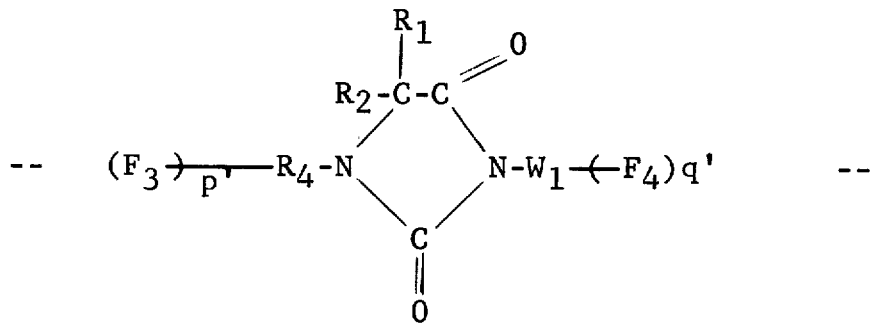

Column 81, delete formula (IV-6) in its entirety and insert the following therefor:

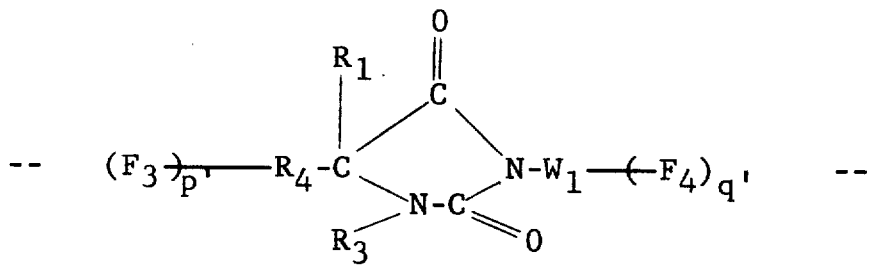

Column 82, delete formula (IV-8) in its entirety and insert the following therefor:

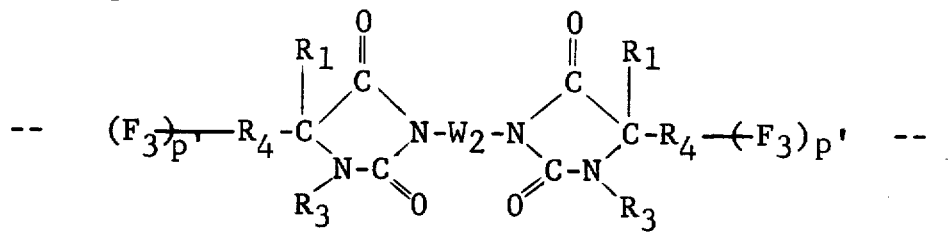

Signed and Sealed this

Tenth Day of August 1976

[SEAL]

Attest:

RUTH C. MASON     C. MARSHALL DANN